(12) United States Patent
Leng et al.

(10) Patent No.: US 12,156,563 B2
(45) Date of Patent: Dec. 3, 2024

(54) HEADGEAR

(71) Applicant: RESMED ASIA PTE. LTD., Singapore (SG)

(72) Inventors: Wai Hoong Leng, Singapore (SG); Mohankumar Krishnan Valiyambath, Singapore (SG); Amit Arunchandra Jadhav, Singapore (SG); Angelene Marie Ozolins, Sydney (AU)

(73) Assignee: ResMed Asia Pte. Ltd., Singapore (SG)

( * ) Notice: Subject to any disclaimer, the term of this patent is extended or adjusted under 35 U.S.C. 154(b) by 0 days.

(21) Appl. No.: 18/029,085

(22) PCT Filed: Sep. 30, 2021

(86) PCT No.: PCT/SG2021/050590
§ 371 (c)(1),
(2) Date: Mar. 28, 2023

(87) PCT Pub. No.: WO2022/071885
PCT Pub. Date: Apr. 7, 2022

(65) Prior Publication Data
US 2023/0284726 A1    Sep. 14, 2023

(30) Foreign Application Priority Data

Sep. 30, 2020    (SG) .............................. 10202009714P

(51) Int. Cl.
*A42B 3/16* (2006.01)
*A42B 1/0188* (2021.01)
(Continued)

(52) U.S. Cl.
CPC ............ *A42B 3/163* (2013.01); *A42B 1/0188* (2021.01); *A61F 11/12* (2013.01); *A61F 11/14* (2013.01);
(Continued)

(58) Field of Classification Search
CPC .............................. A42B 3/163; A42B 1/0188
See application file for complete search history.

(56) References Cited

U.S. PATENT DOCUMENTS 2,893,011 A    7/1959  Finken et al.
3,594,815 A  *  7/1971  Reese .................. A42B 1/0188
                                                2/909
(Continued)

FOREIGN PATENT DOCUMENTS

WO    WO 98/004310 A1    2/1998
WO    WO 98/034665 A1    8/1998
(Continued)

OTHER PUBLICATIONS

"Respiratory Physiology", by John B. West, Lippincott Williams & Wilkins, 9th edition published 2012 (8 pages).
(Continued)

*Primary Examiner* — Khaled Annis
(74) *Attorney, Agent, or Firm* — Nixon & Vanderhye P.C.

(57) ABSTRACT

A headgear includes a pair of noise reduction components. Each noise reduction component is configured to fit over and/or at least partially inside respective ears of a user of the headgear. The pair of noise reduction components are coupled to a first strap. The first strap is configured to retain the pair of noise-reduction components in contact with the ears of the user. Each noise reduction component of the pair of noise reduction components includes a laminated structure that includes at least one sound-reflecting layer, and at least one sound-absorbing layer that is arranged to be closer to the ear of the user than the at least one sound-reflecting layer.

34 Claims, 18 Drawing Sheets

(51) Int. Cl.
*A61F 11/12* (2006.01)
*A61F 11/14* (2006.01)
*A61M 21/02* (2006.01)
*H04R 1/10* (2006.01)

(52) U.S. Cl.
CPC ..... *A61M 21/02* (2013.01); *A61M 2205/3303* (2013.01); *H04R 1/1083* (2013.01)

(56) References Cited

U.S. PATENT DOCUMENTS

| | | | |
|---|---|---|---|
| 3,795,014 A | 3/1974 | Simpson et al. | |
| 4,037,273 A * | 7/1977 | Labaire | A61F 11/14 2/209 |
| 4,302,635 A * | 11/1981 | Jacobsen | H04R 1/1058 381/378 |
| 4,782,832 A | 11/1988 | Trimble et al. | |
| 4,944,310 A | 7/1990 | Sullivan | |
| 5,456,703 A * | 10/1995 | Beeuwkes, III | A61F 11/06 607/114 |
| 5,504,945 A * | 4/1996 | Purnell | A63B 71/10 2/209 |
| 5,687,715 A | 11/1997 | Landis | |
| 6,016,574 A * | 1/2000 | Chen | A45D 8/36 2/209 |
| 6,466,681 B1 * | 10/2002 | Siska, Jr. | H04R 5/0335 381/372 |
| 6,532,959 B1 | 3/2003 | Berthon-Jones | |
| 6,581,594 B1 | 6/2003 | Drew et al. | |
| 6,724,906 B2 * | 4/2004 | Naksen | H04R 1/1066 381/370 |
| 7,866,944 B2 | 1/2011 | Kenyon et al. | |
| 8,204,265 B2 * | 6/2012 | Siskin | A61F 11/14 381/74 |
| 8,636,479 B2 | 1/2014 | Kenyon et al. | |
| 8,638,014 B2 | 1/2014 | Sears et al. | |
| 8,733,349 B2 | 5/2014 | Bath et al. | |
| 8,755,555 B2 * | 6/2014 | Dougherty | H04R 1/1066 381/370 |
| 8,769,723 B1 * | 7/2014 | Ilges | A42B 1/046 2/172 |
| 9,467,767 B2 * | 10/2016 | Chen | H04R 5/033 |
| 10,244,299 B2 * | 3/2019 | Besgen, Sr. | A42B 1/0182 |
| 10,413,696 B2 * | 9/2019 | Kimock | A61M 16/0683 |
| 10,779,604 B2 * | 9/2020 | Lebel | A42B 3/16 |
| 11,172,859 B2 * | 11/2021 | Connor | A61B 5/6814 |
| 11,185,447 B2 * | 11/2021 | Kimock | B05D 5/02 |
| 11,412,328 B2 * | 8/2022 | Kamimura | H04R 1/1008 |
| 11,765,493 B2 * | 9/2023 | Hui | H04R 1/025 381/334 |
| 11,806,214 B2 * | 11/2023 | Kimock | A61F 11/14 |
| 2002/0002733 A1 * | 1/2002 | Keen | A63B 71/10 2/425 |
| 2007/0044205 A1 * | 3/2007 | Sato | A61F 11/14 2/209 |
| 2008/0264715 A1 * | 10/2008 | Leong | A61F 11/08 181/135 |
| 2009/0013447 A1 * | 1/2009 | Drosihn | A42B 1/0188 2/209 |
| 2009/0044808 A1 | 2/2009 | Guney Memduh et al. | |
| 2009/0050156 A1 | 2/2009 | Ng et al. | |
| 2009/0144885 A1 * | 6/2009 | Mix | A42B 1/12 2/209.13 |
| 2009/0178177 A1 * | 7/2009 | Fairclough | A42B 1/0188 2/209 |
| 2009/0205900 A1 | 8/2009 | Purcell et al. | |
| 2010/0000534 A1 | 1/2010 | Kooij et al. | |
| 2011/0170702 A1 * | 7/2011 | Bays | H04R 5/0335 381/74 |
| 2013/0133671 A1 * | 5/2013 | Fairclough | A61F 11/14 2/209 |
| 2013/0243235 A1 * | 9/2013 | Clayton | H04R 1/105 381/371 |
| 2016/0323664 A1 * | 11/2016 | Kirsch | H04R 1/1008 |
| 2017/0099539 A1 * | 4/2017 | Di Censo | G05D 23/00 |
| 2017/0264984 A1 * | 9/2017 | Pelland | H04R 5/0335 |
| 2018/0262825 A1 | 9/2018 | Boyer et al. | |
| 2019/0110931 A1 * | 4/2019 | King | A61F 11/14 |
| 2019/0343686 A1 * | 11/2019 | King | A61F 7/007 |
| 2019/0374386 A1 | 12/2019 | Halfaker | |
| 2020/0100938 A1 * | 4/2020 | King | A61F 7/10 |
| 2020/0289325 A1 | 9/2020 | Kimock et al. | |
| 2020/0296501 A1 * | 9/2020 | Freeman | H04R 1/1083 |
| 2021/0330014 A1 * | 10/2021 | Kim | A42B 1/008 |
| 2022/0130362 A1 * | 4/2022 | Washburn | G10K 11/168 |
| 2022/0167701 A1 * | 6/2022 | McCarthy | A61F 11/14 |
| 2023/0284726 A1 * | 9/2023 | Leng | A42B 1/0188 |

FOREIGN PATENT DOCUMENTS

| | | |
|---|---|---|
| WO | WO 00/38772 A1 | 7/2000 |
| WO | WO 00/78381 A1 | 12/2000 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2009/052560 A1 | 4/2009 |
| WO | WO 2010/135785 A1 | 12/2010 |
| WO | WO 2012/171072 A1 | 12/2012 |
| WO | WO 2013/020167 A1 | 2/2013 |

OTHER PUBLICATIONS

International Preliminary Report on Patentability dated Jan. 12, 2023 issued in International Application No. PCT/SG2021/050590 (29 pages).

International Search Report dated Nov. 8, 2021 issued in International Application No. PCT/SG2021/050590 (5 pages).

Written Opinion of the International Searching Authority dated Nov. 8, 2021 issued in International Application No. PCT/SG2021/050590 (6 pages).

Written Opinion of the International Preliminary Examining Authority dated Aug. 26, 2022 issued in International Application No. PCT/SG2021/050590 (9 pages).

* cited by examiner

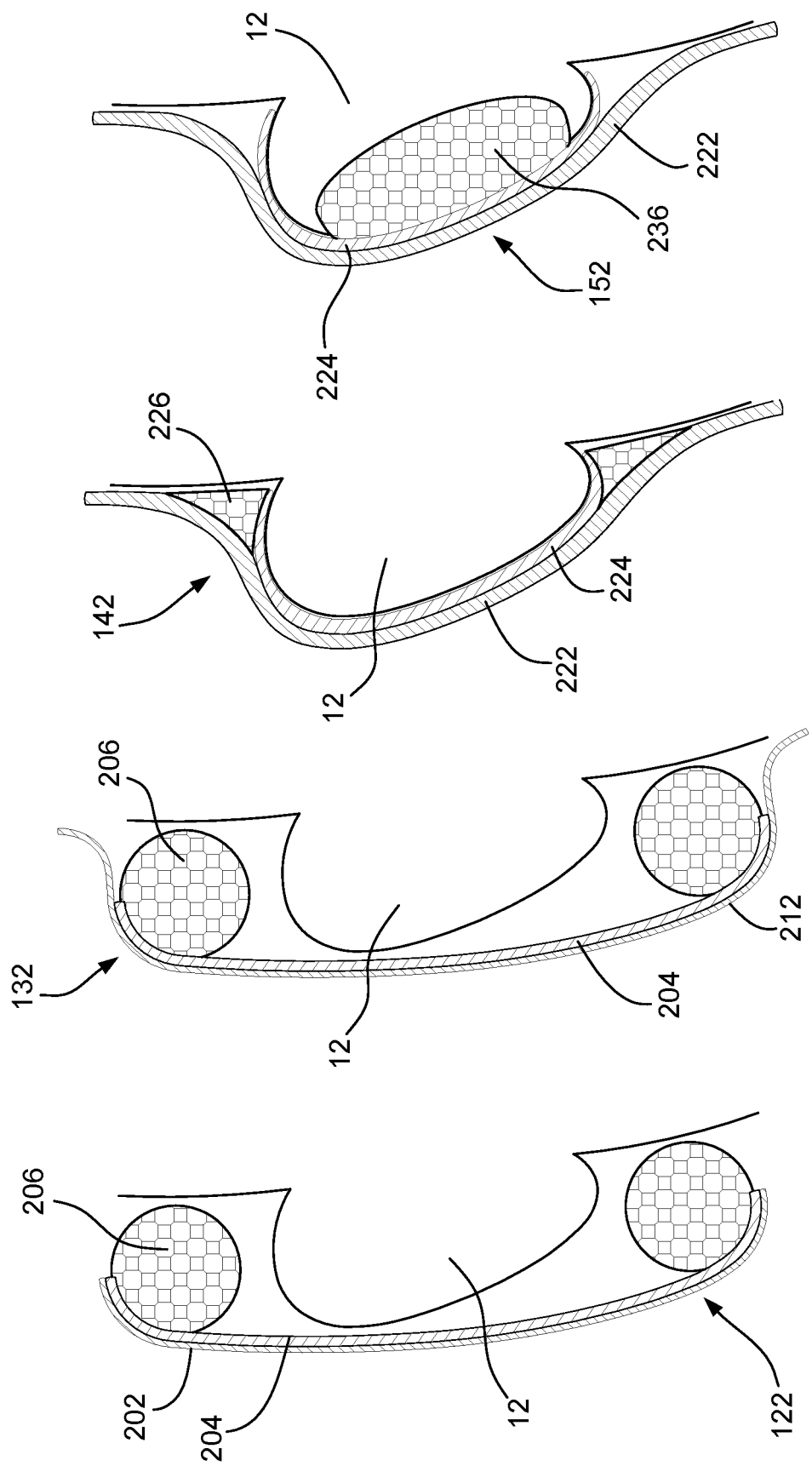

HEADGEAR

CROSS-REFERENCE TO RELATED APPLICATIONS

This application is the U.S. national phase of International Application No. PCT/SG2021/050590 filed Sep. 30, 2021 which designated the U.S. and claims priority to Singapore Provisional application Ser. No. 10202009714P, filed Sep. 30, 2020, the entire contents of each of which are hereby incorporated by reference.

TECHNICAL FIELD

The present disclosure relates to headgear with noise-reducing capabilities, and to noise-reducing components suitable for use with the headgear.

BACKGROUND

A range of respiratory disorders exist. Certain disorders may be characterised by particular events, e.g. apneas, hypopneas, and hyperpneas.

Examples of respiratory disorders include Obstructive Sleep Apnea (OSA), Central Sleep Apnea (CSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Central Sleep Apnea (CSA) is another sleep-related disorder in which the effort to breathe is diminished or absent, typically for 10 to 30 seconds either intermittently or in cycles, and is usually associated with a reduction in blood oxygen saturation.

Treatment of respiratory disorders such as CSA or OSA may be achieved by various respiratory therapies, such as Continuous Positive Airway Pressure (CPAP) therapy, Non-invasive ventilation (NIV), Invasive ventilation (IV), and High Flow Therapy (HFT).

For example, in CPAP therapy, continuous positive airway pressure acts as a pneumatic splint and may prevent upper airway occlusion, such as by pushing the soft palate and tongue forward and away from the posterior oropharyngeal wall. Systems for CPAP therapy may include a patient interface with a seal-forming structure that is held in contact with the patient's face to deliver a flow of air from a flow generator of a CPAP machine at the desired therapeutic pressure. A seal-forming structure may be, or may comprise, a nasal mask, a full-face mask, a nasal pillow, a nasal puff, or an oro-nasal mask.

A common issue that arises when a patient undergoes CPAP therapy is that noise can be generated by various sources including the flow generator, air leakage from the mask, and poor mask ventilation. Further, if a patient temporarily stops using the CPAP machine for some reason, such as discomfort, this may result in loud snoring. It may also, of course, be the case that an OSA or CSA sufferer who has not yet been diagnosed, and who thus has not started CPAP therapy, is susceptible to such loud snoring. These sources of noise can be particularly troublesome for the patient's bed partner, whose own sleep may be disturbed as a result. Other environmental noise sources such as construction work or traffic noise may also contribute to sleep disturbances.

In view of the above issue, a person suffering from sleep disturbances may look to some existing products for relief, such as noise-cancelling earphones or headphones, earplugs, or earmuffs. However, each of these has drawbacks. Earphones and headphones are uncomfortable when worn for extended periods and may need recharging. Earplugs are effective, small and lightweight, but may cause ear infections and can be easily misplaced. Earmuffs are comfortable, but ineffective for noise-cancellation, and may not be comfortable in side sleep.

A further issue that may arise is that the level of noise may be sufficient to disturb a person's sleep, but not sufficient to wake them such that they realise that the disturbance is occurring. It is thus possible that sleep disturbances can affect quality of sleep (for example, by causing a shift from deep sleep to light sleep) whilst going undetected.

It would be desirable to address or alleviate one or more of the above difficulties, or at least to provide a useful alternative.

SUMMARY

The present invention provides a headgear, comprising:
  a pair of noise reduction components configured to fit over and/or at least partially inside respective ears of a user of the headgear, the pair of noise reduction components being coupled to a first strap, wherein the first strap is configured to retain the pair of noise-reduction components in contact with the ears of the user;
  wherein each noise reduction component comprises a laminated structure that comprises at least one sound-reflecting layer, and at least one sound-absorbing layer that is arranged to be closer to the ear of the user than the at least one sound-reflecting layer.

The at least one sound-reflecting layer blocks or reflects external sound from entering the ear, while the at least one sound-absorbing layer acts to reduce sound within a space, such as within the ear of the user. The at least one sound-absorbing layer can reduce the reverberation time, echoes, or prevent the focusing of sound that is reflected from curved surfaces such as the inner or external surfaces of the ear. Accordingly, the reflective layer acts as a first barrier to prevent sound getting through and into the ear, while residual sound between the ear and the noise reduction component will be reduced by the absorption material which is closer to the ear.

In some forms of the present technology, the first strap is resilient along at least part of its length. For example, the first strap may comprise one or more resilient sections and one or more non-stretchable sections.

In some forms, the first strap is formed by at least two separable sections that are movable relative to each other by way of a resilient member.

In some forms, the noise reduction components are integrated with the first strap to form ear-covering portions thereof.

In some forms of the present technology, the noise reduction components are removably connected to the headgear. For example, the noise reduction components may be connected to the headgear via a hook-and-loop fastening mechanism, one or more magnets, and/or one or more clips.

In some forms, the noise reduction components are located at respective ends of a second strap that is coupled to the first strap. For example, the second strap may comprise loops at the respective ends thereof, and the first strap may be configured to be threaded through the loops.

In some forms, the respective ends of the second strap are coupled to the first strap by a pivoting connection.

In some forms of the present technology, the first strap comprises at least one bifurcation, such that a primary portion of the first strap is configured to engage with a forehead of the user, and one or more secondary portions of the first strap are configured to engage with a crown and/or chin of the user.

In some forms of the present technology, the first strap comprises at least one layer of a non-woven textile material.

In some forms of the present technology, the laminated structure comprises at least one layer of a non-woven textile material.

In some forms of the present technology, the at least one layer of a non-woven textile material is directly connected to the at least one sound-absorbing layer.

In some forms of the present technology, the at least one sound-absorbing layer comprises at least one layer of a sound-absorbing foam material. The sound-absorbing foam material may be selected from one or more of: PE closed-cell foam; thermoplastic polyurethane foam; unbroken loop (UBL) fabric; UBL foam laminate; memory foam; EVA foam sheet; and fabric-foam-TPU-PU foam laminate.

In some forms of the present technology, the at least one sound-reflecting layer comprises at least one of: a polymer film; a metallised polymer film; a metallised fabric; and/or a non-woven material.

In some forms of the present technology, the laminated structure comprises at least one lamination layer constructed from a polyurethane film.

In some forms, the headgear comprises one or more electronic components for monitoring, diagnosing and/or treating the user, the one or more electronic components being provided in, or on, the first strap and/or, if applicable, the second strap.

The one or more electronic components may comprise one or more sensors and/or one or more actuators. For example, at least one sensor and/or at least one actuator may be partly exposed to ambient at an exterior surface of the headgear; and/or may be partly exposed at a user-contacting surface of the headgear.

In some forms of the present technology, at least one sensor and/or at least one actuator is at least partly embedded between an outer layer and a user-contacting layer of the headgear.

In some forms of the present technology, at least one sensor and/or at least one actuator comprises circuitry that is at least partially formed by one or more conductive threads, and/or one or more conductive ink traces.

In some forms of the present technology, the one or more electronic components comprise a wireless communications interface for transmitting data from the one or more sensors to one or more external computing devices, and/or for receiving data at the one or more actuators from the one or more external computing devices.

In some forms of the present technology, the one or more sensors and/or one or more actuators comprise one or more of: an accelerometer; a gyroscope; a humidity sensor; a temperature sensor; a microphone; a camera; a pulse oximeter; an EEG sensor; an EMG sensor; an EOG sensor; a touch sensor; a vibration device; and an audio output device.

In some forms of the present technology, the pair of noise reduction components are each larger than adjacent portions of the first strap, and/or the pair of noise reduction components each protrude from a surface of the first strap.

In some forms of the present technology, the at least one sound-reflecting layer directly contacts the at least one sound-absorbing layer. The at least one sound-reflecting layer includes a first sound-reflecting layer and a second sound-reflecting layer. The at least one sound-absorbing layer is sandwiched between the first and second sound reflecting layers.

In some forms of the present technology, the at least one sound-reflecting layer directly contacts the at least one sound-absorbing layer. the at least one sound-reflecting layer is a first sound-reflecting layer and a second sound-reflecting layer, the first sound-reflecting layer is sandwiched between the second sound-reflecting layer and the at least one sound-absorbing layer.

In another aspect, the present invention provides a noise reduction component attachable to headgear wearable by a user, the noise reduction component comprising:

a laminated structure that comprises at least one sound-reflecting layer, and at least one sound-absorbing layer that is arranged to be closer to an ear of the user than the at least one sound-reflecting layer;

wherein the noise reduction component is configured to fit over and/or at least partially inside the ear of the user of the headgear, and wherein the noise reduction component comprises an attachment mechanism to couple the noise reduction component to the headgear, whereby the first strap is configured in use to retain the noise-reduction component in contact with the ear of the user.

The attachment mechanism may comprise a hook-and-loop fastening mechanism, one or more magnets, and/or one or more clips.

In some forms of the present technology, the laminated structure comprises at least one layer of a non-woven textile material.

In some forms of the present technology, the at least one sound-absorbing layer comprises at least one layer of a sound-absorbing foam material. For example, the sound-absorbing foam material may be selected from one or more of: PE closed-cell foam; thermoplastic polyurethane foam; unbroken loop (UBL) fabric; UBL foam laminate; memory foam; EVA foam sheet; and fabric-foam-TPU-PU foam laminate.

In some forms of the present technology, the at least one sound-reflecting layer comprises at least one of: a polymer film; a metallised polymer film; a metallised fabric; and/or a non-woven material.

In some forms of the present technology, the at least one sound-reflecting layer directly contacts the at least one sound-absorbing layer. The at least one sound-reflecting layer includes a first sound-reflecting layer and a second sound-reflecting layer. The at least one sound-absorbing layer is sandwiched between the first and second sound reflecting layers.

In some forms of the present technology, the at least one sound-reflecting layer directly contacts the at least one sound-absorbing layer. The at least one sound-reflecting layer is a first sound-reflecting layer and a second sound-reflecting layer, the first sound-reflecting layer is sandwiched between the second sound-reflecting layer and the at least one sound-absorbing layer.

In another aspect, the present invention provides, a pair of noise reduction components configured to fit over and/or at least partially inside respective ears of a user of the headgear, the pair of noise reduction components being coupled to a first strap, wherein the first strap is configured to retain the pair of noise-reduction components in contact with the ears of the user.

In some forms, each noise reduction component comprises a laminated structure.

In some forms, the laminated structure comprises at least one sound-reflecting layer, and at least one sound-absorbing layer that is arranged to be closer to the ear of the user than the at least one sound-reflecting layer.

In another aspect, the present invention provides a strap including one or more electronic components for monitoring, diagnosing and/or treating the user, the one or more electronic components being provided in, or on, the strap.

In some forms, the one or more electronic components is configured to control a noise reduction component connected to the strap.

In some forms of the present technology, the pair of noise reduction components are each larger than adjacent portions of the first strap, and/or the pair of noise reduction components each protrude from a surface of the first strap.

In another aspect, the present invention provides a noise reduction component comprising at least sound reflecting layer and at least one sound absorbing layer.

In some forms of the present technology, the at least one sound-reflecting layer directly contacts the at least one sound-absorbing layer. The at least one sound-reflecting layer includes a first sound-reflecting layer and a second sound-reflecting layer. The at least one sound-absorbing layer is sandwiched between the first and second sound reflecting layers.

In some forms of the present technology, the at least one sound-reflecting layer directly contacts the at least one sound-absorbing layer. The at least one sound-reflecting layer is a first sound-reflecting layer and a second sound-reflecting layer, the first sound-reflecting layer is sandwiched between the second sound-reflecting layer and the at least one sound-absorbing layer.

In some forms of the present technology, at least one non-woven material is directly in contact with the at least one sound absorbing layer. The non-woven material is capable of effectively reflecting and/or absorbing sound.

In some forms of the present technology, the non-woven material may comprise one or more different types of non-woven material to form a multi-layer non-woven material. The one or more different types of non-woven material may include natural fibres and/or synthetic fibres such as polyester fibres. Various methods may be used to manufacture the non-woven material. For instance, the multi-layered non-woven material may be manufactured by airlaid or spunbond process, or a Spunbond-Meltblown-Spunbond (SMS) process. The non-woven material may comprise ultra-fine fibres, fine fibres and/or fibres with high surface area. Advantageously, the non-woven material is capable of effectively reflecting and/or absorbing sound. Fibres with high surface area may include engineered fibres having various cross-sectional geometry, such as trilobal or multilobal. The non-woven material may have a fibre density and/or fibre architecture (such as how the fibres are arranged in a cross-section of non-woven matrix) that is particularly amenable to sound reflection and/or sound absorption.

In some forms of the present technology, the at least one non-woven material is a first non-woven material and a second non-woven material. A cushioning layer is provided between the first and second non-woven layers. Each layer may contribute to absorption and/or reflection.

In some forms of the present technology, at least one laminate directly in contact with the at least one non-woven material.

BRIEF DESCRIPTION OF THE DRAWINGS

Some embodiments of a headgear, in accordance with present teachings will now be described, by way of non-limiting example only, with reference to the accompanying drawings in which:

FIGS. 2A-2D show schematic cross-sectional views of example configurations of noise-reducing components according to some forms of the present technology;

DETAILED DESCRIPTION

Figure 1:
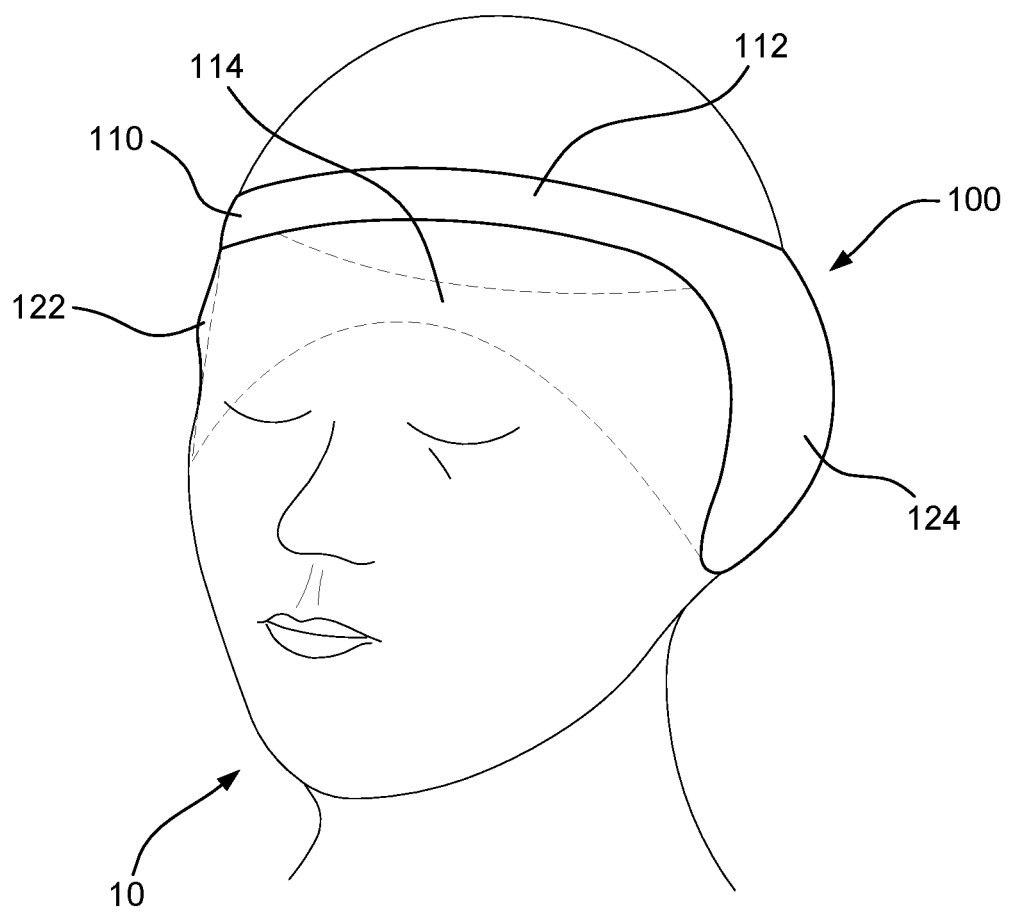
FIG. 1 shows headgear according to one form of the present technology.

Referring initially to FIG. 1, a headgear 100 worn by a user 10 (depicted in partial transparency to enable certain structural features of the headgear 100 to be shown) comprises a strap 110 that, when worn, is retained about the head of the user 10. In particular, the strap 110 comprises a front section 112 that engages with the forehead (e.g., an area overlaying the user's frontal bone) of the user 10 when worn, and a rear section 114 that engages with the back of the user's head (e.g., overlaying the occipital bone), and/or with the user's neck (e.g., overlaying the trapezius muscle).

The headgear 100 also comprises a pair of noise reduction components 122 and 124 located at opposed sides thereof, and being configured to fit over the respective ears of the user 10. In some forms of the present technology, part of a noise reduction component 122 or 124 may also, or alternatively, fit at least partially inside the ear of a user (e.g., an earbud).

The noise reduction components 122 and 124 are integrated with the strap 110 to form a unitary headband structure. For example, the headgear 100 may comprise a pair of lobe structures that are integral with, and extend from, the strap 110 to house the noise reduction components 122, 124. For example, the headgear 100 may comprise inner and/or outer layers of textile material between which the noise reduction components 122, 124 are sandwiched. It will be appreciated that in some embodiments, the noise reduction components 122, 124 may be detached from the headgear 100.

In some forms, each lobe structure housing the respective noise reduction component 122, 124 may be larger (e.g., wider) than the strap 110. This may create a visual differentiation in order to assist the patient with donning the headgear 100. Additionally, the larger size of the noise reduction components 122, 124 may allow the lobe structure to fit around the user's ear (as illustrated in FIG. 1), while the remainder of the strap 110 may be positioned superior to the user's ears.

At least part of the strap 110 may be resiliently stretchable to enable it to be readily fitted to the user's head, and to accommodate a variety of different head sizes. For example, at least a section of the front portion 112 and/or at least a section of the rear portion 114 may be resilient. In some embodiments, the entirety of the headgear 100 may be stretchable in at least a radial direction.

Each noise reduction component comprises a laminated structure that comprises at least one sound reflecting layer and at least one sound absorbing layer. At least one sound absorbing layer is closer to the ear of the user (when the headgear 100 is worn) than the at least one sound reflecting layer.

In some forms, at least a portion of the strap 110 may be constructed from a different material than the noise reduction components 122, 124. For example, the laminate structure may only be present in the noise reduction components 122, 124, and may not be included in the remained of the strap 110. Similarly, the strap 110 may include an elastic material to assist with stretching to different sized heads. The elastic material may not be present in the noise reduction components 122, 124.

Some example configurations of noise reduction components are shown in FIGS. 2A-2D. In the example of FIG. 2A, the noise reduction component 122 has an outer, sound-reflecting, layer 202, and an inner, sound-absorbing, layer 204. The sound-absorbing layer 204 may be formed from a foam material such as a PE closed cell foam sheet, for example. The sound absorbing layer 204 is attached to an annular cushion 206, that may be formed from memory foam in some examples, and that is shaped to substantially encircle the user's ear (e.g., extend around the helix and the lobule) when the headgear 100 is worn.

The sound-reflecting layer 202 acts to at least partially reflect sound waves from external noise sources. As some sound will in most cases still be transmitted through the sound-reflecting layer 202, the sound-absorbing layer 204 acts to at least partially absorb sound that is transmitted through the sound-reflecting layer 202, while also absorbing sound that is reflected from the surface of the user's ear (e.g., the scapha, the anti-helix, the concha, etc.) following transmission, thus reducing reverberation.

In FIG. 2A, the sound-absorbing layer 204 is of approximately the same two-dimensional shape as the sound-reflecting layer 202. In another example, shown in FIG. 2B, the sound-reflecting layer 212 may extend beyond the sound-absorbing layer 204 to wrap over the user's ear 12 (e.g., around the user's helix and the lobule), thus providing greater reflective surface area to further reduce transmission. In these examples, the sound-reflecting layer 202 and the sound-absorbing layer 204 can be laminated to each other.

In a further example, shown in FIG. 2C, the cushion 226 may have a non-circular cross-section so as to provide a tighter fit of the noise reduction component 142 over the ear 12 (e.g., around the helix and the lobule), and an even greater reflective area for the reflecting layer 222 to be provided. In the illustrated example, the sound absorbing layer 224 may contact the reflecting layer 222. In use, the sound absorbing layer 224 may sit over the user's ear and surround the pinna of the ear (e.g., cupping the ear).

Additionally, the sound absorbing layer 224 may be flexible and/or deformable. In some forms, tension in the straps when the user wears the headgear may cause the sound absorbing layer 224 and/or the sound reflecting layer 222 to deform. This may allow the sound absorbing layer 224 to be positioned at least partially within the ear 12 (e.g., proximate to the concha) while in use. Alternatively, the sound absorbing layer 224 may partially extend into the user's ear without needing to deform.

In some forms, the sound absorbing layer 224 can comprise extensions or flaps configured to engage corresponding with at least the pinna of the ear. As would be made clear from the discussion below, the sound-absorbing layer 224 can further comprise a protrusion that sits at least partially within the ear 12. The protrusion can be in the form of a center protrusion (for example, 359 of FIG. 3F) on a patient facing surface of the noise reduction component. The center protrusion is configured such that the ear encircles the center padding. The center protrusion is configured to extend into a cavity formed by the ear (e.g., within the concha). The center protrusion is sized slightly smaller than the ear cavity so as to fit snuggly within the ear.

The sound absorbing layer 224 can be bonded with an adhesive (such as glue) and/or thermally bonded to the sound reflective layer 222 in a laminating process. The protrusion can be formed by moulding or thermal shaping. Alternatively or in addition, the protrusion may be attached as a separate piece via an adhesive or bonding processes (e.g., thermal, or ultrasonic).

In a yet further example, shown in FIG. 2D, a noise reduction component 152 does not have an annular cushion 206 or 226. Instead, a cushion 236 that is shaped to fit inside the user's ear 12 is provided. This provides sound absorption functionality that is additional to that provided by the sound-absorbing layer 224.

The cushion 236 can contact (e.g., directly contact) the sound absorbing layer 224. For example, the cushion 236 and sound absorbing layer 224 can be stacked relative to each other. The cushion 236 and the sound absorbing layer 224 can frictionally engage each other. In some forms, the cushion 236 can be removable for washing if required. Alternatively, the cushion 236 and sound-absorbing layer 224 can be laminated to each other (via glue lamination or with thermal bonding) such that it fits inside the user's ear as a single entity or unitary body.

In some forms, the sound absorbing layer 224 may be positioned outside of the user's ear, similar to the sound absorbing layer of FIG. 2C (e.g., in order to cup the user's ear). The cushion 236 and sound-absorbing layer 224 can protrude from the sound absorbing layer 224 and extend into a cavity of the ear. The cushion 236 may not need to deform in order to fit within the user's ear, and may be similar to the protrusion 359 of FIG. 3F (described below).

In some forms, the sound-absorbing layer 224 of FIG. 2D can be bonded thermally or with an adhesive (e.g., glue) to the sound reflective layer 222 in a laminating process.

In some alternative forms, the noise reduction component 152 of FIG. 2D may include the annular cushion 226 like in FIG. 2C. Like in FIG. 2C, the cushion may have a non-circular cross-section so as to provide a tighter fit of the noise reduction component 152 over the ear 12 (e.g., around the helix and the lobule).

Referring now to FIGS. 3A-3F, some more detailed example structures of multi-layer noise reduction components are shown.

Figure 3A:
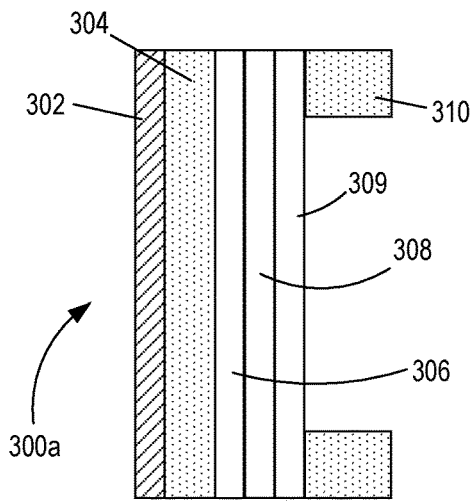
FIGS. 3A-3F show schematic cross-sectional views of example layer structures of noise-reducing components according to some forms of the present technology.

FIG. 3A shows a noise reduction component 300a having the following layers:
- An outer reflecting layer 302, such as an Aluminised PET Sheet.
- An absorbing layer 304, which may be constructed from a foam material such as a PE closed cell foam sheet; this also has a cushioning effect.
- A layer 306 of a non-woven material. The non-woven material may comprise one or more different types of non-woven material to form a multi-layer non-woven material. The one or more different types of non-woven material may include synthetic fibres such as polyester fibres. Various methods may be used to manufacture the non-woven material. For instance, the multi-layered non-woven material may be manufactured by airlaid or spunbond process, or a Spunbond-Meltblown-Spunbond (SMS) process. The non-woven material may comprise fine fibres and/or fibres with high surface area. Advantageously, the non-woven material is capable of effectively reflecting and/or absorbing sound. Fibres with high surface area may include engineered fibres having various cross-sectional geometry, such as trilobal or multilobal. Preferably, the non-woven material may comprise fine fibres which leads to a higher surface area and therefore better sound reflection and sound absorption.
- A lamination layer 308, such as a polyurethane film (e.g. U073) for laminating the non-woven layer 306 to another fabric layer.
- A fabric layer 309, which may be unbroken loop (UBL) fabric, for example. As the fabric layer 309 may contact the user's ear and/or may extend beyond the noise-reduction component 300a to integrate with the headgear, the fabric layer 309 may be designed to have a soft feel to the user's skin for optimal comfort.
- A cushioning layer 310 which may form a rim around a periphery of the noise-reduction component 300a. The rim may be formed from memory foam, for example. The material of the cushioning layer 310 may contact the user's auriculotemporal sulcus and postauricular sulcus to provide comfort on sensitive portions of the user's ear.

Figure 3B:
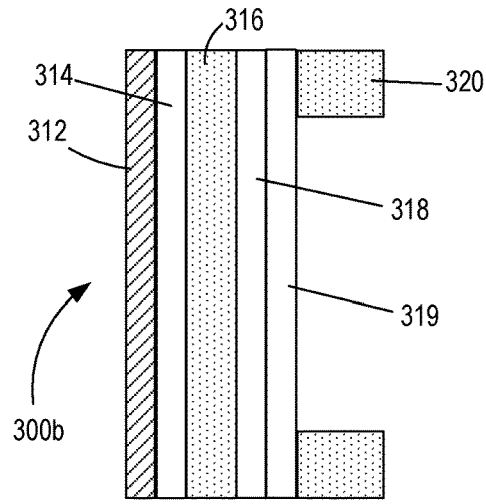

FIG. 3B shows a noise reduction component 300b having the following layers:
- An outer reflective layer 312, for example formed from Aluminised Fabric.
- A first layer 314 of non-woven material, such as that described for layer 306 in FIG. 3A. The non-woven material may have a fibre density and/or fibre architecture (such as how the fibres are arranged in a cross-section of non-woven matrix) that is particularly amenable to sound reflection and/or sound absorption.
- A cushioning layer 316, such as a Foamy Film layer. The cushioning layer 316 may facilitate sound absorption, and may also facilitate lamination of the reflecting and/or absorbing material 314 to other layers.
- A second layer 318 of non-woven material. The second non-woven layer 318 may be identical or similar to the first non-woven layer 314. By providing multiple non-woven layers either side of a foam absorbing layer, the noise-reducing capabilities of the noise-reduction component 300b may be enhanced while maintaining a relatively thin form factor.
- A fabric layer 319, such as UBL fabric (as above).
- A cushioning layer 320, which may form a rim about a periphery of the noise-reduction component 300b as above. The cushioning layer 320 may be formed from memory foam. The material of the cushioning layer 320 may contact the user's auriculotemporal sulcus and postauricular sulcus to provide comfort on sensitive portions of the user's ear.

Figure 3C:
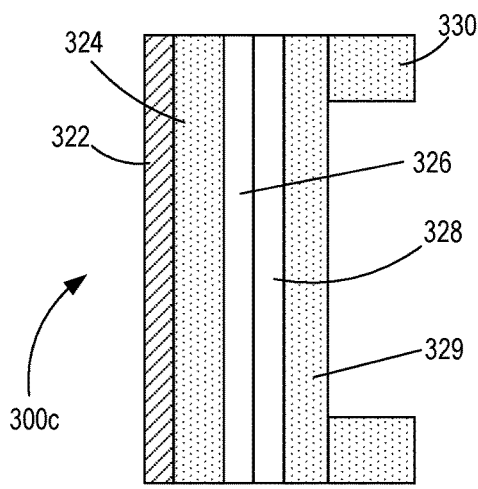

FIG. 3C shows a noise reduction component 300c having the following layers:
- An outer reflective layer 322, for example formed from Aluminised Fabric.
- An absorbing layer 324, for example formed from UBL foam laminate.
- A second reflective layer 326, such as formed from TPU Film. The second reflective layer may also facilitate lamination of the absorbing layer 324 to other layers, such as a fabric layer 328 that may be formed from a UBL fabric.
- A cushioning and absorbing layer 329, such as a layer of Foamy Film.
- A cushioning peripheral layer 330, for example formed from memory Foam. As described above, the cushioning peripheral layer 330 may contact sensitive regions of the user's ear to assist in providing a comfortable fit.

Figure 3D:
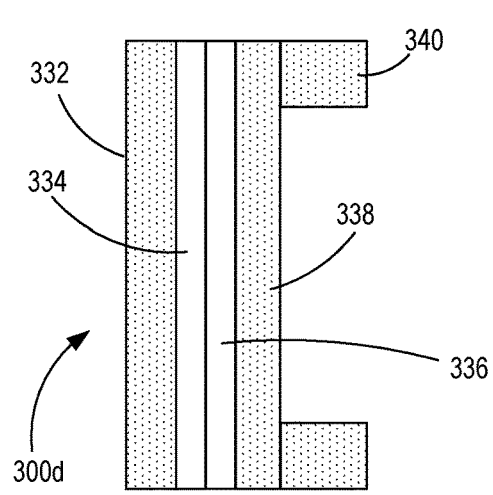

FIG. 3D shows a noise reduction component 300d having the following layers:
- An outer absorbing layer 332 such as an EVA foam sheet layer.
- A first reflecting layer 334 such as a layer of Polypropylene (PP) non-woven material. Alternatively, other non-woven materials comprising natural fibres and/or synthetic fibres may be used.
- A second reflecting layer 336 such as a layer of Polyester non-woven material. Alternatively, other non-woven materials comprising natural fibres and/or synthetic fibres may be used.
- An absorbing and/or reflecting layer 338 such as a Fabric-foam-TPU-PU foam laminate.
- A cushioning peripheral layer 340, for example formed from memory Foam. As described above, the cushioning peripheral layer 340 may contact sensitive regions of the user's ear to assist in providing a comfortable fit.

Figure 3E:
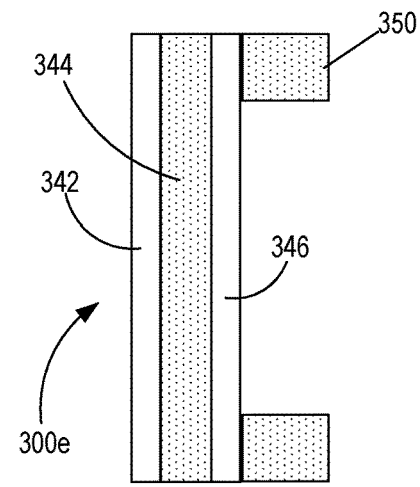

FIG. 3E shows a noise reduction component 300e having the following layers:
- An outer fabric layer 342, for example formed from UBL fabric, which may have sound absorption capability.
- An absorbing layer 344, for example a polyethylene (PE) closed cell foam sheet.
- A reflective layer 346, such as a Polyester non-woven layer. Alternatively, other non-woven materials comprising natural fibres and/or synthetic fibres may be used.
- A cushioning peripheral layer 350, for example formed from memory foam. As described above, the cushioning peripheral layer 350 may contact sensitive regions of the user's ear to assist in providing a comfortable fit.

Figure 3F:
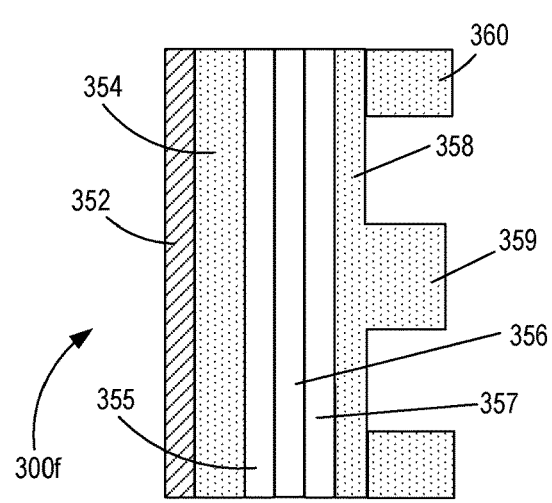

FIG. 3F shows a noise reduction component 300f that is of similar configuration to noise reduction component 300a, but with the addition of a further foam layer 358 having a central protrusion 359 that is shaped to abut against the user's ear to provide additional sound absorption functionality. It will be appreciated that any of the other example noise reduction components 300b, 300c, 300d, 300e could be augmented in like fashion. The noise reduction component 300f has the following layers:

- An outer reflecting layer 352, such as an Aluminised PET Sheet.
- An absorbing layer 354, which may be constructed from a foam material such as a PE closed cell foam sheet; this also has a cushioning effect.
- A layer 355 of a non-woven material. The non-woven material may comprise one or more different types of non-woven material to form a multi-layer non-woven material, such as a tri-layered non-woven material that may be found in a surgical mask. Various methods may be used to manufacture the non-woven material. For instance, the tri-layered non-woven material may be manufactured by SMS process. The non-woven material may have ultra-fine fibres (such as in the range of about 0.5 Denier (D) to about 1.3 D), fine fibres and/or fibres with high surface area. Fibres with high surface area may include engineered fibres having various cross-sectional geometry, such as trilobal or multilobal. Preferably, the non-woven material may have ultra-fine fibres which leads to a higher surface area and therefore better sound reflection and sound absorption.
- A lamination layer 356, such as a polyurethane film (e.g. U073) for laminating the non-woven layer 306 to another fabric layer.
- A fabric layer 357, which may be unbroken loop (UBL) fabric, for example. As the fabric layer 309 may extend beyond the noise-reduction component 300f to integrate with the headgear, the fabric layer 357 may be designed to have a soft feel to the user's skin for optimal comfort.
- A first memory foam layer 358 having a protrusion 359 shaped to nest within the user's ear. For example, the protrusion 359 may fit within the user's concha.
- A cushioning layer 360 which may form a rim around a periphery of the noise-reduction component 300f. The rim may be formed from memory foam, for example. As described above, the cushioning layer 360 may contact sensitive regions of the user's ear to assist in providing a comfortable fit.

The arrangements of layers shown in FIGS. 2A-2D and 3A-3F may each be capable of effectively blocking sound having a frequency of 500 Hz or less, and an intensity of 25 dB or higher.

In some forms of the present technology, a headgear may have one or more sensors and/or actuators provided therein, for measurement of the user's physiological and sleep data. One or more sensors and one or more actuators may respectively be embedded within the headgear, or may be attached to internal and/or external surfaces of the headgear. An example of such a headgear 400 is shown in FIGS. 4 and 5.

Figure 4:
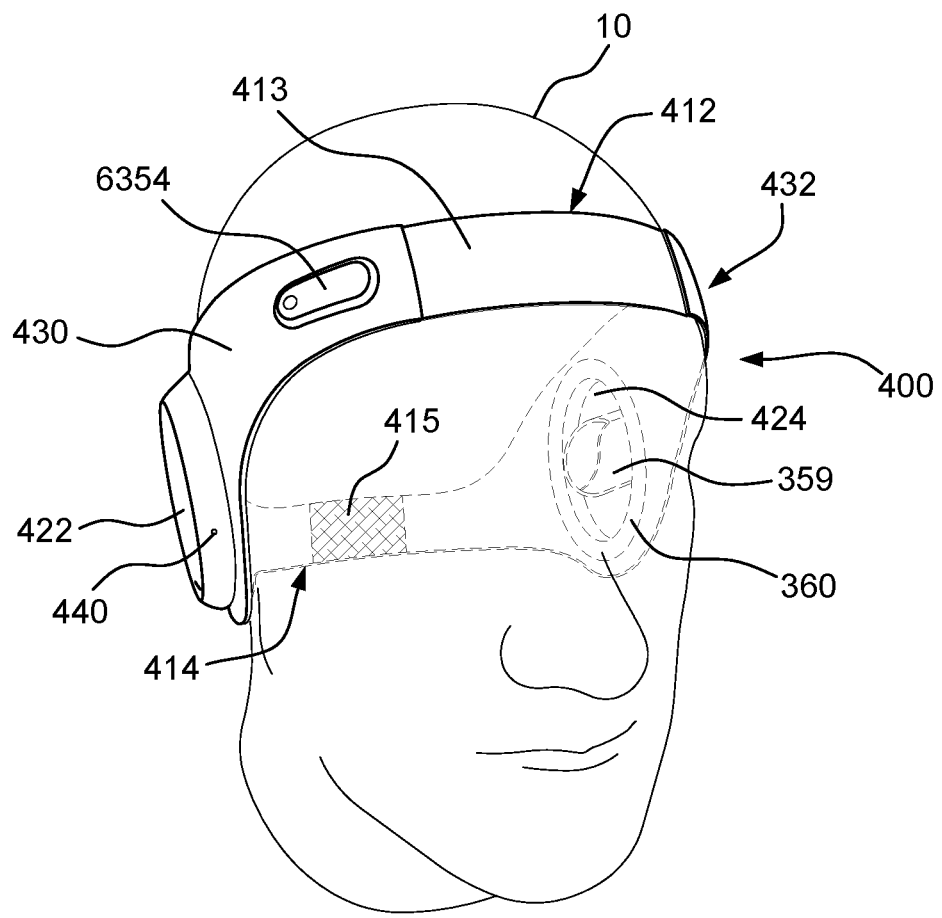
FIG. 4 shows headgear according to another form of the present technology.
Figure 5:
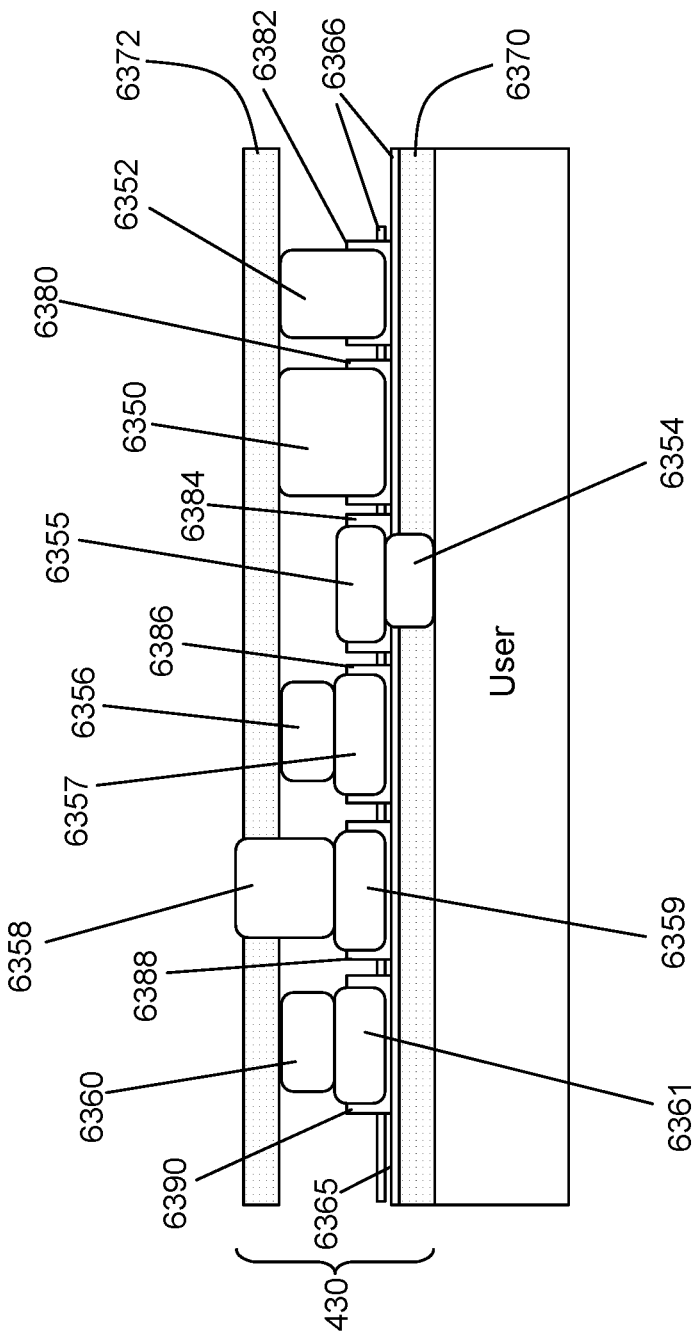
FIG. 5 is a schematic partial cross-section through the headgear of FIG. 5.

Referring to FIG. 4, a smart headgear device 400 comprises a strap that, when worn by a user, is retained about the head of the user. The strap comprises a front section 412 that engages with the forehead (e.g., overlaying the frontal bone) of the user 10 when worn, and a rear section 414 that engages with the back of the user's head (e.g., overlaying the occipital bone), and/or with the user's neck (e.g., overlaying the trapezius muscle). The strap in this embodiment is formed by two non-stretchable parts 430 and 432 that are connected by resilient sections in the form of front elastic band 413 and rear elastic band 415. Each non-stretchable part 430 has a multilayer structure, for example a multilayer configuration according to any of FIG. 2A-2D or 3A-3F. In some embodiments, the resilient sections may be part of a single circumferential elastic band that is a layer of the multilayer structure of the non-stretchable parts 430, 432. That is, further layers of material are provided on one or both surfaces of the elastic band to rigidify it to form the non-stretchable parts 430, 432, while leaving sections 413, 415 of the elastic band exposed such that they remain stretchable and resilient.

The headgear 400 also comprises a pair of noise reduction components 422 and 424 located at opposed sides thereof, and being configured to fit over the respective ears of the user 10. For example, the noise reduction components 442 and 424 may fit around both the helix and the lobule of the respective ear. In some embodiments, at least part of the noise reduction component 422 or 424 may fit inside the user's ear (e.g., within the concha), such as the sound-absorbing foam protrusion 359 of noise reduction component 424.

In some forms, the noise reduction components 422, 424 may be larger (e.g., wider) than adjacent portions of the front section 412 and/or rear section 414 of the strap. This may reduce the total contact area on the user's head, while also allowing the noise reduction components 422, 424 to be wide enough to extend around the user's ears.

In some forms, the noise reduction components 422, 424 may protrude further outwardly (e.g., in a lateral direction from the user's head) than the adjacent portions of the front section 412 and/or the rear section 414 of the strap. This may provide adequate space to receive the user's ears.

The noise reduction components 422 and 424 are integrated with respective non-stretchable parts 430, 432 of the strap to form a unitary headband structure. Each non-stretchable part 430, 432 comprises a lobe structure that houses the noise reduction components 422, 424. For example, the lobe structure may comprise inner and outer layers between which the noise reduction components 422, 424 are sandwiched. Alternatively, the lobe structure may comprise means for releasably attaching the noise-reduction components 422 or 424 to the headgear, for example by hook-and-loop fasteners, clips, a snap-fit connection, magnets that are located in the noise-reduction components and in the headgear, and the like.

In some forms of the present technology, a microphone 440 may be integrated into the noise reduction component 422 or 424 to collect data on external noise. The noise data may be correlated with data from other sensors that are integrated into the headgear 400, such as EEG sensor 6254, to enable assessment of the effect of external data on sleep. One or more such sensors, and other electronic components such as actuators, transceivers and the like, may be integrated into non-stretchable parts 430, 432 in a manner which will be described in more detail below.

Advantageously, sensors embedded in the headgear can help collect sleep-related data and physiological indicators such as vital data; this can be used to determine sleep quality, and may also be used to control one or more integrated actuators or external devices to assist in improving sleep quality. The physiological and sleep data may be communicated (e.g., via wireless communication) to external computing devices such as a smartphone of the patient, and/or a monitoring server that is operated by or accessible to a clinician or other healthcare provider.

In some embodiments, it may be advantageous for the noise-reduction components 422, 424 to be detachable from the headgear 400 so that the user can use the headgear 400 on its own to record data such as brain activity and environmental data including external noise and movement while suffering with sleep interruption. This enables the user to show the effect of the environmental data on brain activity and thus sleep quality. Further, the user is able to see quantitative evidence of the effect of wearing the noise-reduction components 422, 424 on sleep quality, to support qualitative observations from their personal experience.

Referring to FIG. 5, non-stretchable part 430 may have a plurality of electronic modules (actuators and/or sensors) 6354, 6356, 6358 and 6360 integrated therein. A processor module 6350 may also be integrated in the headgear 400, typically also in non-stretchable part 430, though it will be appreciated that the processor module 6350 may be located elsewhere such as in the other non-stretchable part 432. The processor module 6350 may have an integrated transceiver for transmitting data to, and receiving data from, external computing devices. An electrical energy storage device such as a battery 6352 may also be included to power the various electronic components (sensors/actuators 6354-6360 and processor module 6350) of the headgear 400. In some forms of the present technology, other electrical energy storage devices such as supercapacitors may be used.

By integrating the electronic modules into the non-stretchable part 430, when compared to the use of stretchable circuits formed from conductive threads and the like, it is possible to minimise the risk of any electronic components being damaged when the stretchable parts of headgear 400 are stretched to enable the user to fit the headgear 400 snugly in place.

As shown in FIG. 5, the sensors and associated electronics may be integrated at least partly between fabric layers of the non-stretchable part 430. For example, various sensor/actuator modules and/or associated circuitry, the processor module 6350, and the battery module 6352 may lie between an inner, skin-contacting, fabric layer 6370, and an outer fabric layer 6372.

The sensor and/or actuator modules integrated in the headgear 430 may be in electrical communication with processor 6350 and battery 6352 via a bus 6365, for example. The bus 6365 may be provided between two insulating layers 6366 that provide electrical insulation and that also prevent moisture ingress, for example from perspiration absorbed by inner fabric layer 6370. The insulating layers 6366 may be non-conductive polymer or elastomer films, for example, though it will be appreciated that other electrically insulating materials may also be used.

In some forms of the present technology, a thermally insulating layer may be provided between at least some of the electronic components of the positioning and stabilising structure 6300, noting that those components will tend to generate heat during use. Accordingly, a thermally insulating layer helps to improve user comfort. For example, layer 6366 that is closest to the patient-contacting inner layer 6370 may be thermally insulating as well as electrically insulating, or an additional thermally insulating layer may be interposed between electrically insulating layer 6366 and inner layer 6370. In some examples, inner layer 6370 may itself be thermally insulating.

In some forms of the present technology, the sensor and/or actuator modules 6354-6360 and their associated circuitry, and other modules including the processor 6350 and battery 6352, may be received within retaining structures 6380-6390 that are affixed to insulating layer 6366 and/or inner fabric layer 6370. Each retaining structure 6380-6390 is in electrical communication with bus 6365, for example, and may contain electrical contacts to electrically connect circuitry of (or associated with) the sensor modules to bus 6365, and thus also to battery 6352 and processor 6350. In some examples, communication between modules 6350-6360 and bus 6365 may be via conductive ink traces, and/or conductive threads that are woven into or otherwise integrated with fabric layers 6370 and/or 6372. In some embodiments, electrical contacts and/or circuit traces may be contained only in outer layer 6372, so as not to be affected by perspiration from the user.

In some examples, the modules 6350-6360 may be detachable from the sensor-retaining structures 6380-6390, such that particular modules may be switched out for other modules with different functionality, or to replace modules that have ceased to function or are at the end of their lifecycle. For example, the modules 6350-6360 (and/or the circuitry modules 6355, 6357, 6359 and 6361 to which they are electrically coupled, if applicable) may releasably attach to the sensor-retaining structures 6380-6390. To this end, an external surface of a module may form a friction fit with an internal surface of a wall of a sensor-retaining structure 6380-6390, or may form a snap fit, such as an annular snap fit or cantilever snap fit, with the wall or other internal or external part of the sensor-retaining structure. In some embodiments, a non-mechanical coupling, such as magnetic coupling, may be used to retain the modules 6350-6360 in respective retaining structures 6380-6390.

In some forms of the present technology, retaining structures 6380-6390 may comprise pockets formed in the non-stretchable part 430 (for example, by making incisions in outer layer 6372 or inner layer 6370), into which modules 6350-6360 (or their associated circuitry) are insertable to electrically couple with the bus 6365.

Battery module 6352 may comprise a rechargeable battery. The battery may be recharged by connecting it to an external power source, for example via a micro-USB or USB-C port of the battery module 6352 (the port being exposed via outer fabric layer 6372, for example), or by inductive charging. In some embodiments, the battery 6352 may be a disposable battery, for example disposed within a pocket 6382 of the non-stretchable part 430, and may be removable by the user for replacement with a fresh battery.

In some forms of the present technology, one or more sensor modules and/or actuator modules may be enclosed entirely between the fabric layers 6370, 6372, such that no part of the one or more sensor modules is exposed. For example, an actuator module 6360 may be coupled to associated circuitry 6361 that is received in a sensor-retaining structure 6390. Both the actuator module 6360 and circuitry 6361 lie entirely between the fabric layers 6370, 6372. In another example, a sensor module 6356 and associated circuitry 6357 may lie entirely between fabric layers 6370, 6372. One example of a sensor module 6356 that may be fully embedded is an accelerometer or gyroscope.

In some forms of the present technology, a sensor module or actuator module may be at least partly exposed. For example, a humidity sensor 6358 coupled to circuitry 6359 may be at least partly exposed to ambient through the outer fabric layer 6372 to measure humidity of the user's environment. To this end, outer fabric layer 6372 may comprise an aperture through which a surface of the humidity sensor 6358 may be exposed. In another example, a sensor 6354 coupled to circuitry 6355 may have a surface thereof exposed through the inner fabric layer 6370 (e.g., through an aperture formed therein), such that the sensor surface can contact the skin of the user when the headgear 400 is worn by the patient. The sensor 6354 may be a pulse oximeter, for example.

Although the electronic components are described above as being modular in construction, and in at least some cases able to be switched out for other components, in some forms of the present technology, one or more electronic components (such as sensors or actuators) may be woven or otherwise integrated into the material of the non-stretchable part 430, for example into the outer fabric layer 6372 or the inner fabric layer 6370, and/or into another part of the headgear 400, such as the other non-stretchable part 432, or even into the resilient sections 413, 415. This may enable distribution of a sensor over a larger area for more informative and/or accurate measurements to be made.

Some forms of the present technology may comprise one or more sensors for determining sleeping position and movements of a user. In some forms, the determined sleeping position and movements may be used to provide a sensory stimulus to the user to cause them to change position. For example, if a number of apnea and/or hypopnea events above a certain threshold, and/or a decrease in blood oxygenation, is detected by the one or more sensors, this may be indicative of back sleeping. One or more actuators may receive an activation signal based on the detection, and the activation signal may cause the one or more actuators to generate a vibration or other tactile stimulus to irritate the user sufficiently to cause them to switch to another sleeping position.

For example, headgear 400 may incorporate an accelerometer and/or gyroscope. The accelerometer and/or gyroscope may be fully enclosed between fabric layers 6370 and 6372 of the first non-stretchable part 430, for example as shown at 6360 in FIG. 5.

In some forms of the present technology, accelerometer and/or gyroscope measurements may be used to determine a sleep stage of the user.

In some forms of the present technology, a pulse oximeter incorporated in the headgear 400 may be used to assess sleep health. For example, a pulse oximeter 6354 and associated circuitry 6355 may be incorporated in the first non-stretchable part 430, as shown in FIG. 5. The pulse oximeter 6354 is exposed through an aperture of inner fabric layer 6370 such that it can contact the skin of the patient's forehead. Measurements recorded by pulse oximeter 6354 may be used to determine blood oxygen saturation level and heart rate during the period that the headgear 400 is worn, and this data may be transmitted an external computing device such as a smartphone, other mobile computing device, or laptop or desktop computing system of the user. This communication may occur wirelessly (e.g., using Wi-Fi), although wired communication may also occur. The time series data may be consolidated to provide feedback to the user on their health levels, and recommendations for follow-up (for example, by a clinician).

In one example, an Apnea Hypopnea Index (AHI), which is a measure that clinicians use to classify the severity of sleep apnea, may be determined based on sensor measurements. Computation of AHI may use a combination of data from different sensors, e.g. blood oxygen level and heart rate (for example, measured by a PPG sensor), and chest movement (for example, measured by an accelerometer and/or gyroscope). The AHI value may be used to determine when an "apnea" occurs.

Accordingly, by tracking the AHI over time, a clinician will be able to tell if the user has sleep apnea, and provide details of how severe it is. Further, by analysis of the AHI data together with other sensor data, the clinician may be able to not only correlate the frequency of apneas with particular sleeping positions (e.g. sleeping on back or sleeping on side), but also potentially to prescribe CPAP therapy for the user.

In some forms of the present technology, an EEG sensor may be provided in headgear 400, for example in first non-stretchable part 430. The EEG sensor may be partially exposed in the manner shown at 6354 in FIG. 5 such that it can contact the skin of the patient's forehead. Typically, the EEG sensor comprises a plurality of EEG electrodes that generate signals that may be analysed to detect sleep stages. The signals may be transmitted (via transceiver 6350) to an external device, such as the patient's smartphone, and the sleep stage, cycle and duration information may be used to provide feedback to the user on how sleep quality, as well as recommendations for enhanced health. For example, the EEG sensor measurements may be used for accurate sleep staging, to enable a more accurate determination of when an apnea or arousal from sleep occurs, e.g. during a sleep study.

In some forms of the present technology, the sleep stage information may be used to activate sleep-enhancing white/pink noise, and/or binaural beats. These may be produced by audio devices embedded in the headgear 400 itself, or by external devices that receive trigger signals from the headgear 400 via transceiver 6350. For example, one or more miniature bone-conduction speakers may be incorporated in noise reduction components 422 and/or 424.

In some forms of the present technology, a headgear 430 may incorporate electromyography (EMG) and/or electrooculography (EOG) sensors. EMG and EOG sensor signals may be analysed to determine REM sleep stage occurrences. In similar fashion to examples that incorporate EEG sensors, the sleep stage information determined by the EMG/EOG sensors may be used to provide feedback to the patient on sleep quality, or to activate one or more audio devices to produce sleep-enhancing noise.

At least some of the EMG/EOG sensors may be incorporated in first non-stretchable part 430. For example, a ground electrode and reference electrode may be provided in the front section of the first non-stretchable part 430, and exposed through respective apertures in inner layer 6370 so as to be able to contact the patient's forehead. In another example, a ground electrode may be provided in a rear section of the first non-stretchable part 430, or in noise reduction component 422 such that the ground electrode sits behind the user's ear in use. Further electrodes may be provided, each having a cable that attaches to and/or extends within headgear 400 at one end, and to an external electrode patch at the other end, the electrode patch being positionable by the user on the temple and below their eye to provide two additional measurement channels.

In some forms of the present technology, a combination of sensors and actuators may be provided to effect localised temperature change to improve user comfort. For example, an EEG sensor and/or pulse oximeter may be provided in first non-stretchable part 430 (for example in the manner shown at 6354 in FIG. 5), and a temperature sensor and/or a humidity sensor may also be provided in first non-stretchable part 430 (for example in the manner shown at 6358 in FIG. 5). Signals from the EEG and/or PPG sensors may be analysed to detect sleep state, and signals from the temperature sensor and/or humidity sensor may be used to assess ambient comfort levels. One or more Peltier elements may be provided, for example in wearable form on a wristband, and may be coupled to circuitry that communicates with the EEG/PPG and temperature/humidity sensors to receive signals indicative of sleep state and ambient comfort level, and that causes the Peltier element to be activated to locally warm or cool the body (e.g. at the wrist) to help the patient remain in a comfortable sleep state.

In some forms of the present technology, a haptic feedback element (such as a miniature vibratory motor) may be incorporated in the headgear 400, for example in a temple region of the headgear 400. The haptic feedback element may deliver vibrations to the patient to produce a calming effect. For example, processor 6350 may monitor heart rate data from a pulse oximeter 6354, and if this exceeds a threshold, transmit a trigger signal to the haptic feedback element to cause it to vibrate at a few beats lower than the patient's current heart rate, to help slow it down. In another example, as mentioned above, a haptic feedback element may be used to influence the sleeping position of the user if it is detected that they are in a sleeping position that is correlated with apnea or hypopnea events.

In some forms of the present technology, one or more miniature thermo electric generators (TEGs) may be incorporated into the headgear 400, such that the difference between the patient's body temperature and the ambient temperature may be used to generate a potential difference and thus to provide power to the various electronic components (sensors, actuators, processor, etc.) of the headgear 400. For example, miniature TEGs may be located in the first non-stretchable part 430 and/or the second non-stretchable part 432, and exposed through an aperture of the inner layer 6370 such that they contact the patient's forehead.

In some forms of the present technology, multiple sensors may be incorporated in a single module. For example, an accelerometer and gyroscope may be incorporated in a single package.

Screening, Diagnosis, Monitoring Systems

At least some forms of the present technology allow for screening, diagnosis and/or monitoring of sleep health using sensors incorporated in headgear.

For example, as mentioned, a sensor-enabled headgear may be worn by the user, and sensor measurements recorded during sleep. The sensor measurements may be used to accurately monitor sleep stages and sleeping positions, to track vital signs and other physiological indicators, and to detect apnea and/or hypopnea events. The sleep data and physiological data may be used by clinicians to diagnose sleep disorders and to recommend appropriate therapy. Further, the same parameters may be monitored by like sensors integrated in a patient interface during CPAP therapy, and compared to the parameters prior to commencing therapy (or at an earlier stage of therapy) to enable the patient and the clinician to assess the efficacy of the therapy.

As mentioned, physiological and sleep data may be recorded by one or more sensors of the headgear 400, and communicated to external computing devices such as a smartphone of the patient, and/or a monitoring server that is operated by or accessible to a clinician or other healthcare provider.

In some forms of the present technology, a pulse oximeter incorporated in the headgear 400 may be used to determine blood oxygen saturation level and heart rate during the period that the headgear 400 is worn, and this data may be transmitted to an external computing device such as a smartphone, other mobile computing device, or laptop or desktop computing system of the user. The time series data may be consolidated to provide feedback to the user on their health levels, and recommendations for follow-up (for example, by a clinician), for example based on determination of an AHI as discussed above, which can be used in conjunction with other sensor measurements to determine when and how often apnea events are occurring, and an optimal treatment regimen for the user.

Other sensors which may be incorporated in a screening, diagnosis and/or monitoring system that comprises a sensor-enabled headgear include, without limitation: an EEG sensor for detection of sleep stages; EMG and EOG sensors for determining REM sleep stage occurrences; a microphone for detecting snoring or other sounds indicative of disturbed sleep.

Some example applications of sensor-enabled headgear will now be described.

Polysomnography

Polysomnography (PSG) is a monitoring process that typically involves a variety of different sensors and associated equipment, and that can be challenging to set up, even for an expert. A typical PSG system comprises a headbox which receives and records signals from the following sensors: an EOG electrode; an EEG electrode; an ECG electrode; a submental EMG electrode; a snore sensor; a respiratory inductance plethysmogram (respiratory effort sensor) on a chest band; a respiratory inductance plethysmogram (respiratory effort sensor) on an abdominal band; an oro-nasal cannula with oral thermistor; a photoplethysmograph (pulse oximeter); and a body position sensor. The electrical signals are referred to a ground electrode (ISOG) positioned in the centre of the forehead.

A sensor-enabled headgear, such as headgear 400, can replace some or all of the functions of an existing PSG system, since, as discussed above, some or all of the sensors used by a PSG system can be provided in the headgear 400. For example, EOG, EEG, ECG and EMG electrodes, a microphone (acting as a snore sensor), a PPG sensor, and an accelerometer and/or gyroscope (acting as body position sensor(s)) can all be provided in non-stretchable parts 430 and/or 432. A ground electrode may also be provided as described above.

By integrating the sensors with the headgear 400, in at least some examples, it becomes far more straightforward to implement PSG, since the patient is simply able to don the headgear 400, with no or minimal additional configuration required (e.g., no need to manually place various electrodes for the EEG/EMG/EOG sensors).

Non-Obtrusive Monitoring System

In one example, one or more accelerometers and/or one or more gyroscopes and/or one or more other motion sensors may be provided in the headgear 400. The motion sensor(s) is or are configured to generate one or more signals representing bodily movement of the patient, from which may be obtained a signal representing respiratory movement of the patient.

In addition, one or more sensors may be used to record data relating to environmental noise and/or movement. For example, a microphone may record external sound while one or more infrared motion sensors may record movement of the user's bed partner, and an accelerometer or gyroscope may record the user's own movement. This data may be indicative of sleep interruption and/or causes thereof, and may be associated with other data recorded by sensors of the headgear 400, such as EEG data and the like to determine the effect on sleep quality.

Further examples of different headgear form factors will now be described with reference to FIGS. 6A-6B, 7A-7B, 8A-8C, 9A-9C, 10A-10C, and 11-14.

Referring to FIGS. 6A-6B and 7A-7B, a headgear 600 comprises a first, circumferential, strap having a front section 612 that engages with the forehead of the user 10 when worn, and a rear section 614 that engages with the back of the user's head, or with the user's neck.

The headgear 600 also comprises a pair of noise reduction components 622 and 624 located at opposed sides thereof, and being configured to fit over the respective ears of the user 10. In some forms of the present technology, at least part of a noise reduction component 622 or 624 may also, or alternatively, fit inside the ear of a user.

The noise reduction components 622 and 624 are integrated with the strap at opposed sides thereof, consistent with the configuration of the headgear 400 of FIG. 4. Each noise reduction component 622 or 624 may be configured in accordance with any of FIG. 2A-2D or 3A-3F, for example. In some embodiments, the noise reduction components 622, 624 may be detachable from headgear 600.

The headgear 600 also comprises a second strap 620 that extends between the noise reduction components 622, 624 such that it rests against the crown of the user's head when the headgear 600 is worn. In other words, the second strap 620 may overlay the user's occipital bone and/or the parietal bones. The second strap 620 provides additional support to help ensure that the headgear 600 remains in position, as it resists downward movement that may be caused by movement of the first strap as the user moves during sleep. In some embodiments, the second strap may be integral with the first strap.

In some forms, the noise reduction components 622, 624 may be larger (e.g., wider) than adjacent portions of the front section 612 and/or rear section 614 of the strap. This may reduce the total contact area on the user's head, while also allowing the noise reduction components 622, 624 to be wide enough to extend around the user's ears.

In some forms, the noise reduction components 422, 424 may protrude away from the surface of adjacent portions of the front section 612 and/or the rear section 614 of the strap. This may provide adequate space to receive the user's ears.

Figure 6A:
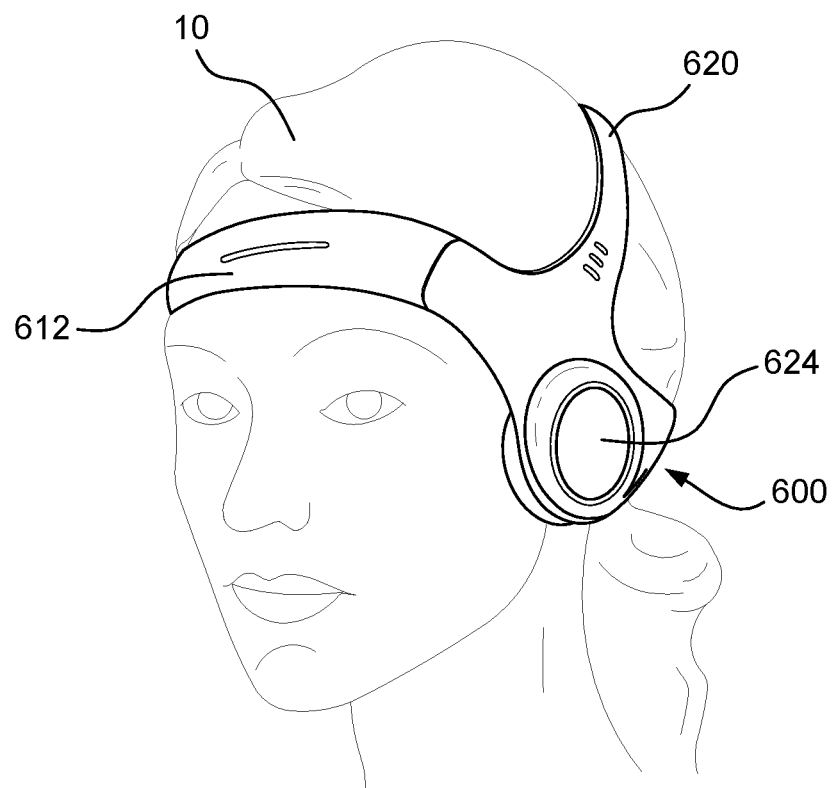
FIGS. 6A and 6B show headgear according to another form of the present technology.
Figure 6B:
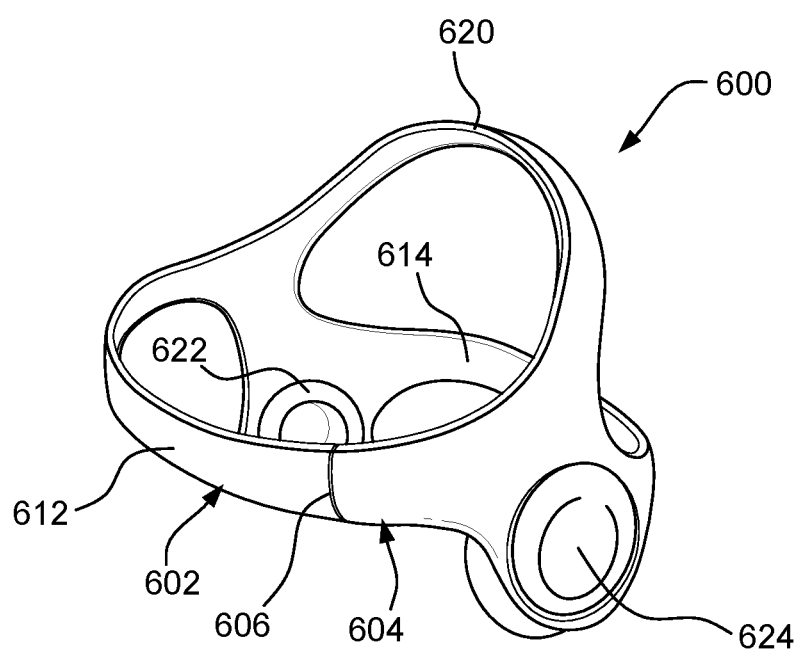

The first strap may be formed from two non-stretchable parts 602 and 604 that are connected by a resilient member 608 (FIG. 7A) that enables the parts to be moved relative to each other by a pulling force but to be urged back together when the pulling force is removed, so as to secure the first strap to the user's head. Accordingly, if the user's head is too large to be accommodated by the default configuration (in which the resilient member 608 is unstretched and the non-stretchable parts abut against each other at join 606 as shown in FIG. 6B), by forcing the headgear 600 downwards to don it, the resilient member 608 enables the headgear 600 to still be fitted comfortably.

Figure 7A:
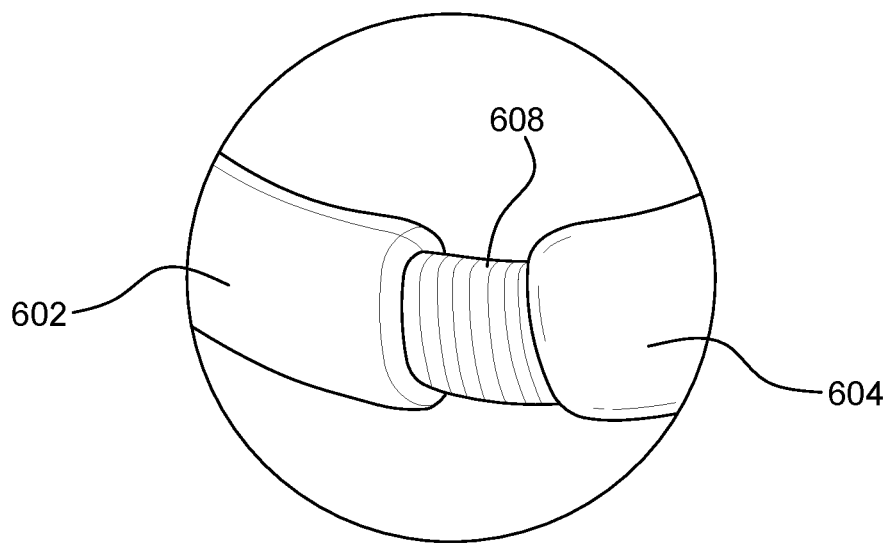
FIG. 7A shows a resilient section of the headgear of FIGS. 6A and 6B.
Figure 7B:
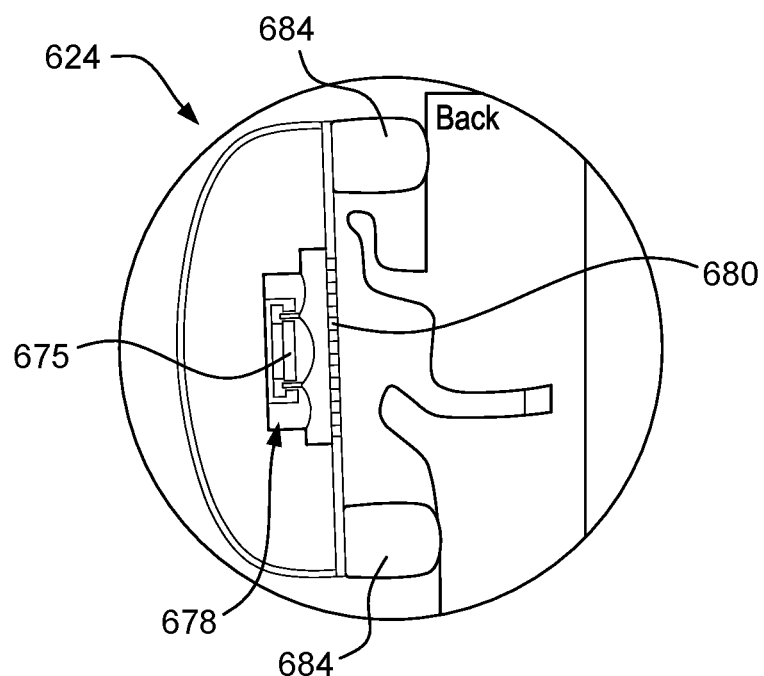
FIG. 7B shows a schematic cross-section through a noise-reducing component of the headgear of FIGS. 6A and 6B.

As illustrated in FIG. 7B, the noise reduction component 624 may include an internal electrical element 675. The internal electrical element 675 may be positioned within the central protrusion (not shown). The internal electrical element 675 may be positioned within a cavity 678, and at least partially covered by a membrane 680. In some forms, the internal electrical element 675 may be a noise sensor for detecting the noise level in the ear. In some forms, the internal electrical element 675 may be a speaker that can output a sound (e.g., white noise, music, sleep meditation) directly from the internal electrical element 675 and/or by communicating with an external device (e.g., a mobile application using wireless communication). The cavity 678 may direct the output noise toward the membrane 680 so that it can be heard by the user. In the illustrated example, the membrane 680 may include holes to allow the sound to pass to the user's ear. A cushioning layer 684 may be provided at an edge of the membrane 684. Although this description is specifically related to the noise reduction component 624, the noise reduction component 622 may include similar structure.

Figure 8A:
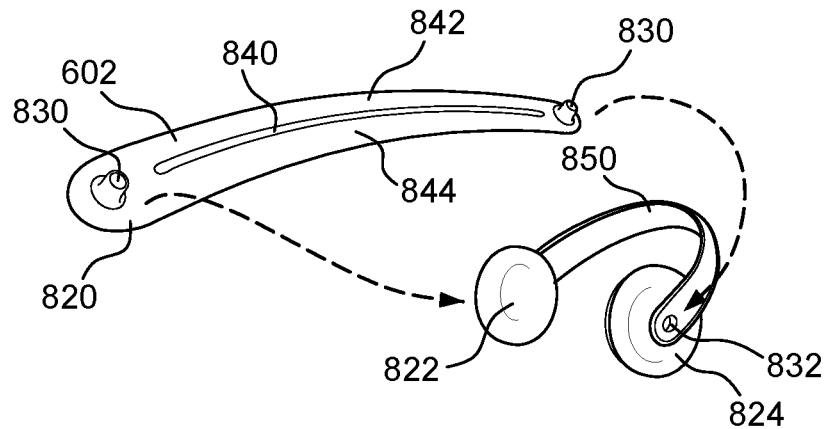
FIGS. 8A-8C show headgear according to another form of the present technology.
Figure 8B:
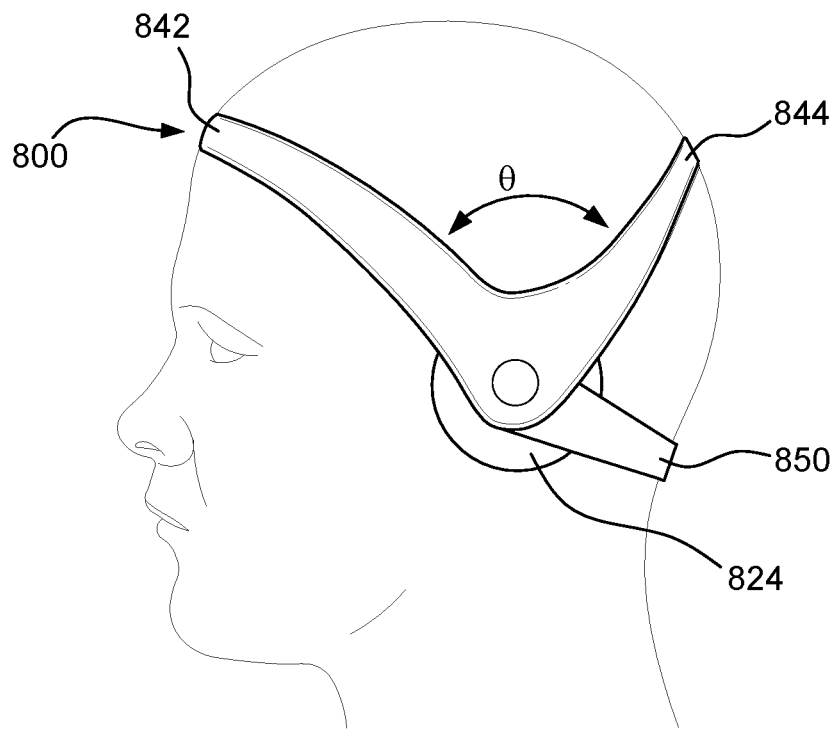
Figure 8C:
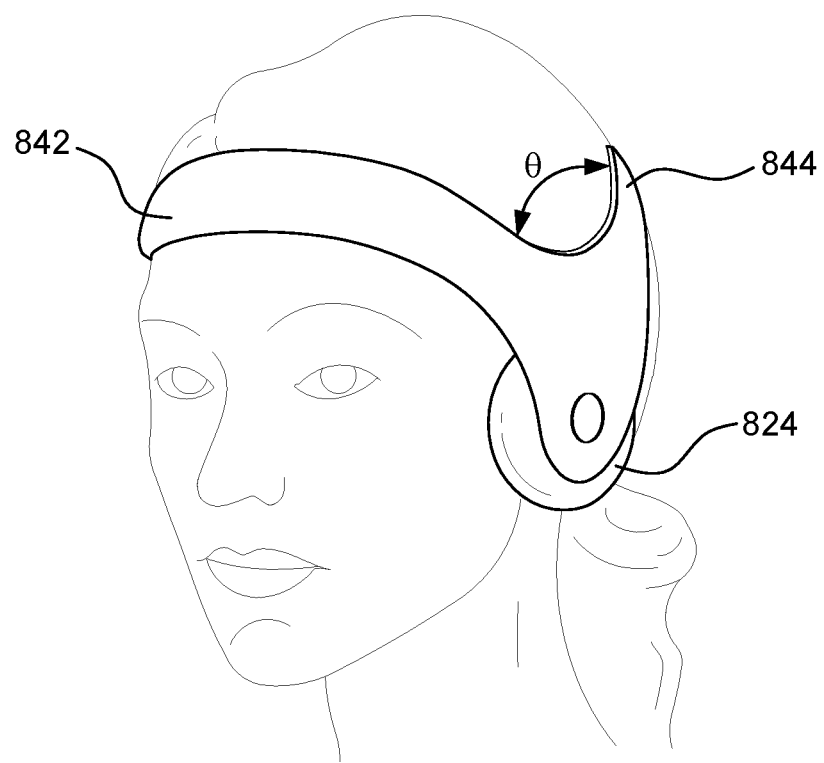

In another example, shown in FIGS. 8A-8C, a headgear 800 comprises a first strap 820 that is bifurcated into a first part 842 and a second part 844. The first strap 820 is connected to a second strap 850, the second strap 850 carrying a pair of noise reduction components 822, 824, by a pivotal connection. For example, the first strap 820 can comprise connectors 830 at each of its ends, and the connectors 830 can attach to corresponding sockets 832 at ends of the second strap 850 in a manner that enables pivoting movement of the second strap 850 relative to the first strap 820.

The bifurcated structure of the first strap 820 is such that, when the first and second straps 820 and 850 are connected to form the headgear 800 and the headgear 800 is worn by a user, the first part 842 of the first strap 820 can engage with the user's forehead while the second part 844 can be pulled away from the first part 842 and positioned on the crown of the user's head. In other words, the first part 842 may overlay the user's frontal bone and the second part 844 may overlay the user's occipital bone and/or the parietal bones. Further, the second strap 850 may be adjusted rotationally to a position at the back of the user's head or neck for optimal fit and comfort. The second strap 850 may overlay the user's occipital bone and/or the trapezius muscle.

In some forms, the first part 842 may be movable to an infinite number of positions relative to the second part 844. For example, an angle θ between the first part 842 and the second part 844 may be any value depending on the size of the user's head and/or a desired position to promote user comfort.

Each of the noise reduction components 822 and 824 may be constructed substantially in accordance with any of the configurations shown in FIGS. 2A-2D or FIGS. 3A-3F.

The first strap 820 and/or the second strap 850 may be resilient along at least part of their lengths such that the headgear 800 is sufficiently supported in engagement with the user's head, with the noise reduction components 822 and 824 retained in place over the user's ears.

In some forms, the noise reduction components 822, 824 may be larger (e.g., wider) than adjacent portions of the first strap 820 and/or second strap 850 of the strap. This may reduce the total contact area on the user's head, while also allowing the noise reduction components 822, 824 to be wide enough to extend around the user's ears.

In some forms, the noise reduction components 822, 824 may protrude away from the surface of adjacent portions of the first strap 820 and/or the second strap 850. This may provide adequate space to receive the user's ears.

Figure 9A:
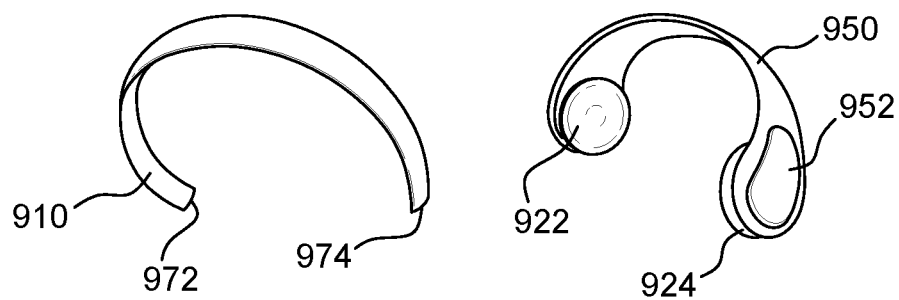
FIGS. 9A-9C show headgear according to a further form of the present technology.
Figure 9B:
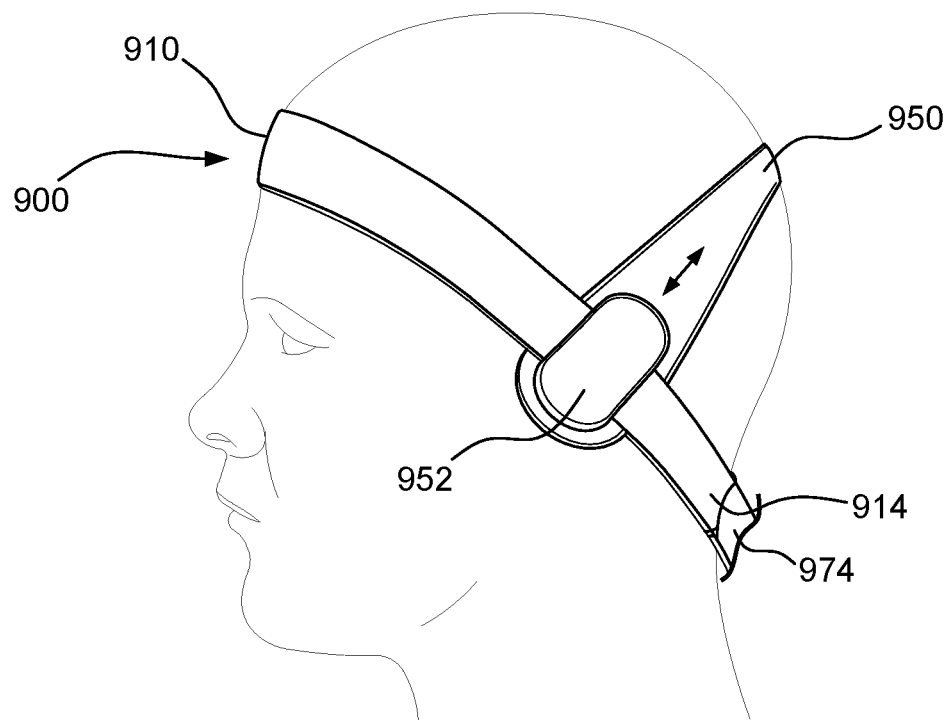
Figure 9C:
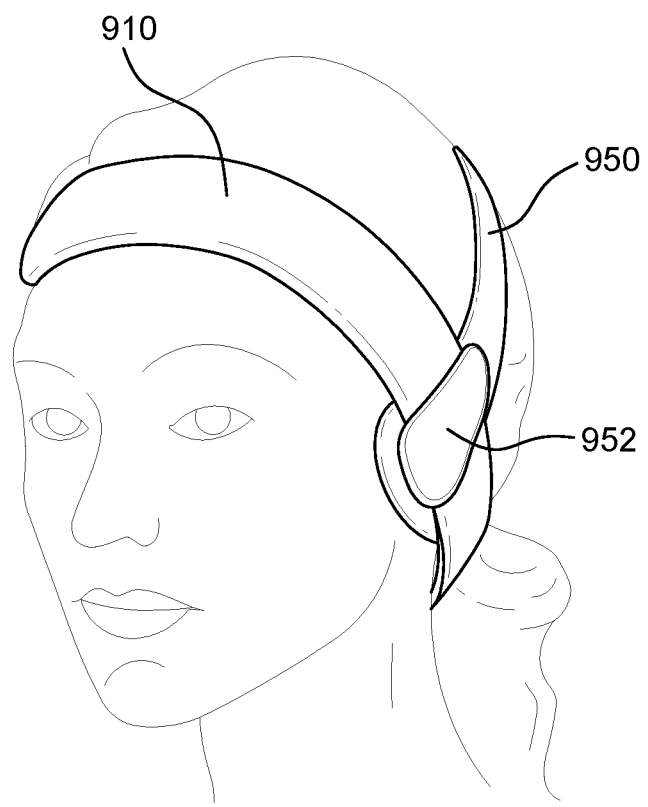

In another example, shown in FIGS. 9A-9C, a headgear 900 comprises a first strap 910 that can be looped through a second strap 950 that carries a pair of noise reduction components 922 and 924 (which may be of like construction to noise reduction components 822 and 824) at respective ends thereof. Respective ends 972, 974 of the first strap 910 are threaded through respective loops 952 at respective ends of an outwardly-facing surface of the second strap 950, and are connected together to form a closed loop. For example, the connection may be by way of one or more sets of hook and loop fasteners. The connection between ends 972, 974 of the first strap 910 may also be made by a buckle, a magnet, a mechanical fastener, using a knot, or any similar connection means. The first strap 910 therefore engages with the user's forehead and neck while the second strap 950 is supported on the crown of the head. For example, FIG. 9B illustrates that the first strap 910 may overlay the user's frontal bone and the second strap 950 may overlay the user's occipital bone and/or the trapezius muscle. For example, the connected ends 972, 974 may form the rear portion 914 for contacting the rear of the user's head.

In some forms, the second strap 950 may be able to stretch when worn by the user. For example, the second strap 950 may be at least partially constructed from an elastomeric material. As illustrated by the arrow in FIG. 9B, the second strap 950 may stretch in order to fit a variety of head sizes (e.g., so that a limited number of sizes may fit a wide range of users). When the user removes the second strap 950, the second strap 950 returns to its initial position.

In some forms, the noise reduction components 922, 924 may be larger (e.g., wider) than adjacent portions of the first strap 910 and/or second strap 950 of the strap. This may reduce the total contact area on the user's head, while also allowing the noise reduction components 922, 924 to be wide enough to extend around the user's ears.

In some forms, the noise reduction components 922, 924 may protrude away from the surface of adjacent portions of the first strap 910 and/or the second strap 950. This may provide adequate space to receive the user's ears.

Figure 10A:
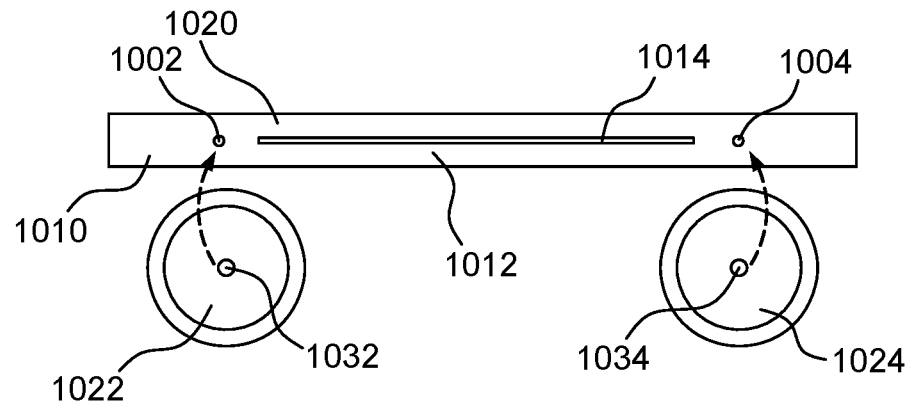
FIGS. 10A-10C show headgear according to a yet further form of the present technology.
Figure 10B:
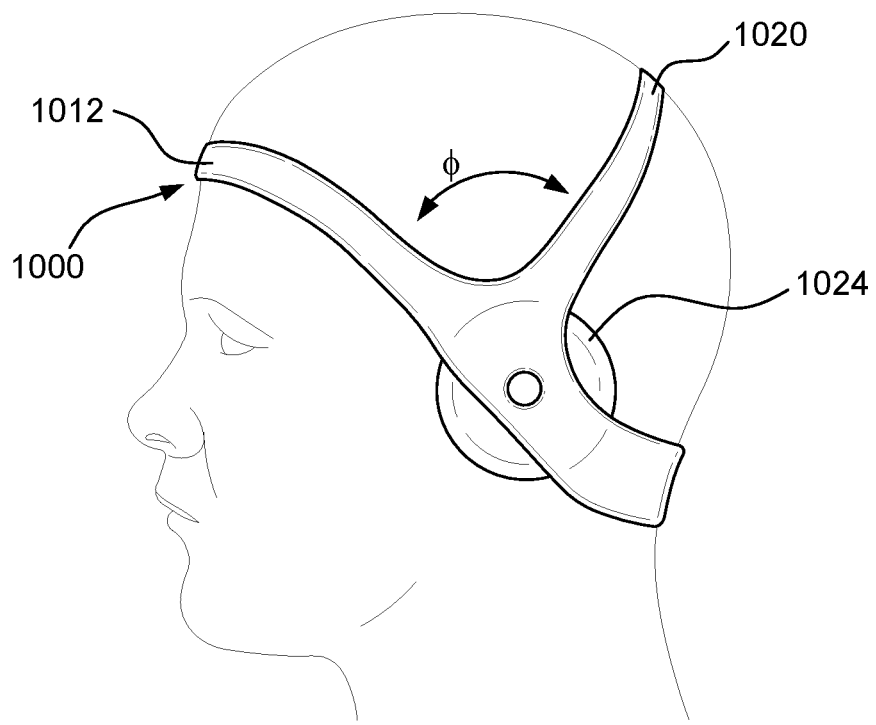
Figure 10C:
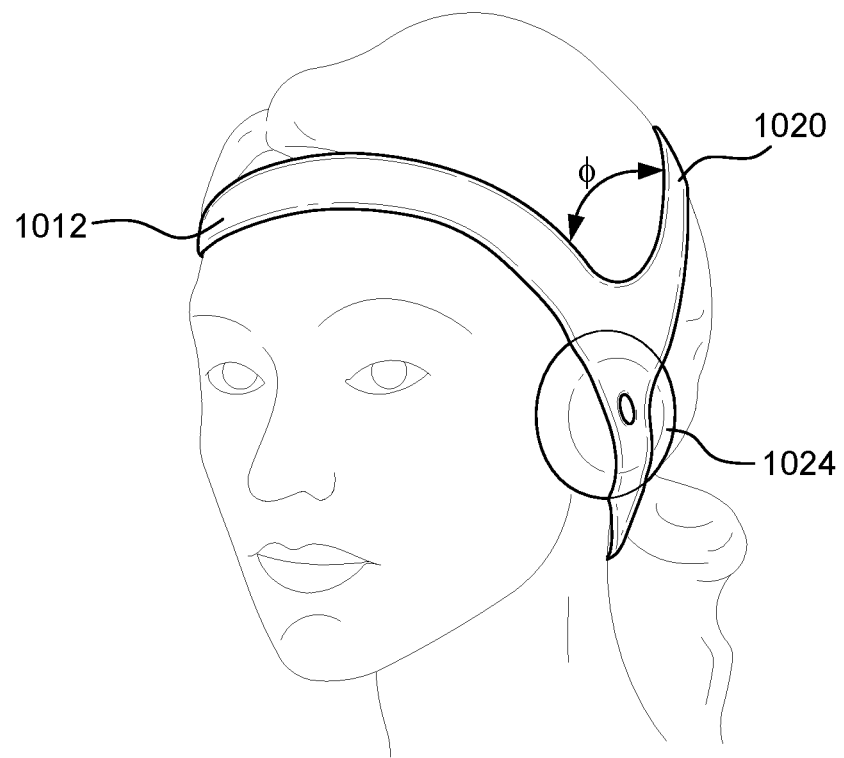

In a further example, shown in FIGS. 10A-10C, a headgear 1000 comprises a single strap 1010 having a bifurcation 1014. The strap 1010 has two apertures 1002, 1004 either side of the bifurcation 1014 that enable connection to respective noise reduction components 1022 and 1024 (which may be of like construction to noise reduction components 822 and 824) via protrusions 1032 and 1034. The strap 1010 is stretchable such that it can fit around a user's head as shown in FIGS. 10B and 10C. Further, the bifurcation 1014 enables a second part 1020 of the strap 1010 to be pulled and stretched away from a first part 1012 of the strap 1010 such that the second part 1020 can provide a crown support (e.g., overlaying the parietal bones and/or the occipital bone) while the first part 1012 engages with the forehead (e.g., overlaying the frontal bone) to provide a forehead support.

In some forms, the first part 1012 may be movable to an infinite number of positions relative to the second part 1020. For example, an angle between the first part 1012 and the second part 1020 (e.g., a bifurcation angle) may be any value depending on the size of the user's head and/or a desired position to promote user comfort.

In some forms, the noise reduction components 1022, 1024 may be larger (e.g., wider) than adjacent portions of the first part 1012 and/or second part 1014 of the strap. This may reduce the total contact area on the user's head, while also allowing the noise reduction components 1022, 1024 to be wide enough to extend around the user's ears.

In some forms, the noise reduction components 1022, 1024 may protrude away from the surface of adjacent portions of the first part 1012 and/or the second part 1014. This may provide adequate space to receive the user's ears.

Figure 11:
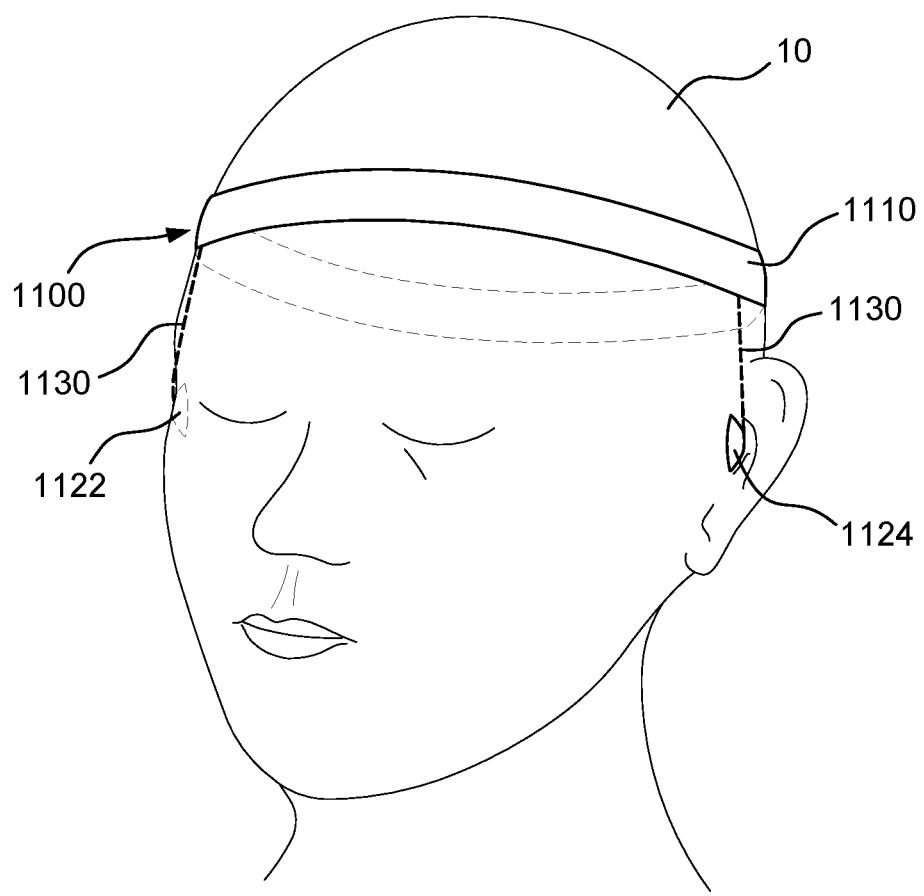
FIG. 11 shows headgear according to another form of the present technology.

In a yet further example, shown in FIG. 11, a headgear 1100 may comprise a single strap 1110 that has a pair of noise reduction components 1122 and 1124 attached thereto by respective elastic tethers 1130. The strap 1110 is resilient and can be stretched to be donned by the user 10, and the noise reduction components 1122 and 1124 then pulled downwards to be inserted into the user 10's ears.

Figure 12:
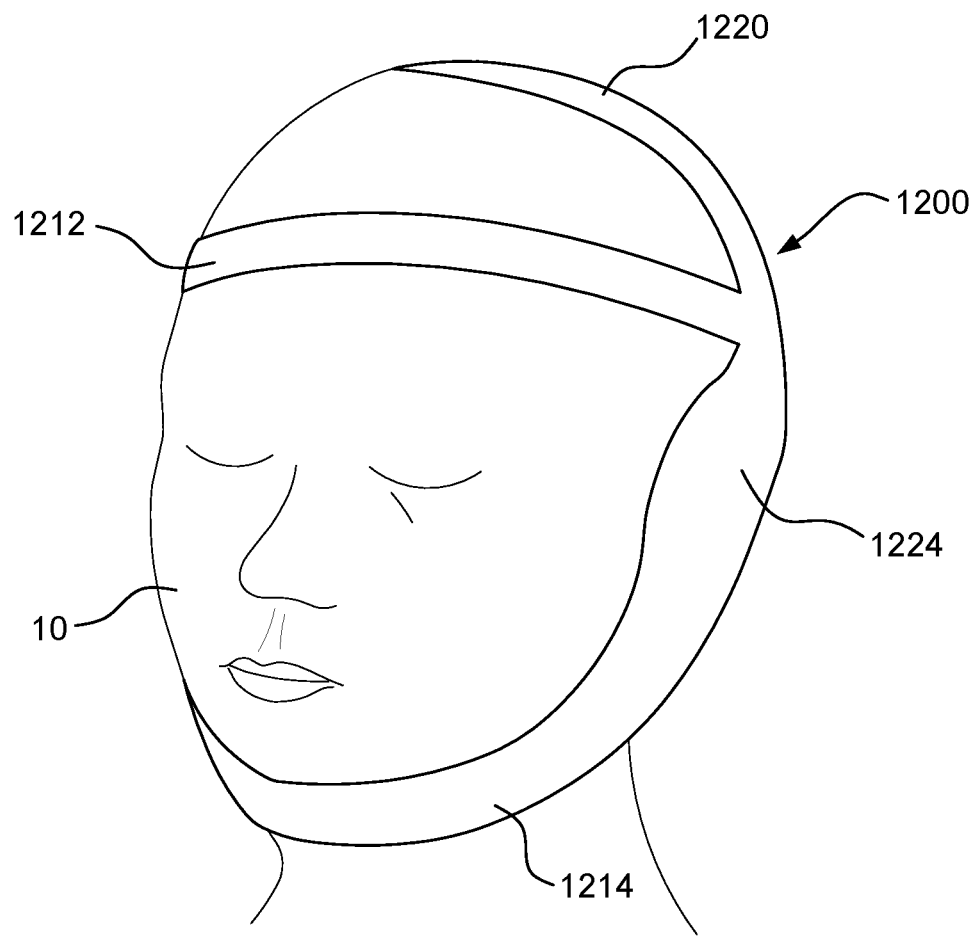
FIG. 12 shows headgear according to another form of the present technology.

In a yet further example, shown in FIG. 12, a headgear 1200 may comprise a strap that is configured to engage with a chin of the user 10. For example, the strap may be stretchable such that a first section 1220 thereof engages with a crown of the user's head (e.g., overlaying the user's parietal bones and/or occipital bone), while a second section 1214, opposite the first section 1220, engages with the user's chin. The user's chin may be considered the portion of the face overlaying the mandible. For example, the user's chin may be proximate to the mental protuberance (e.g., contacting the mental protuberance and/or inferior to the mental protuberance and overlaying the digastricus muscle when the user is in an upright position). The strap may be bifurcated such that a third section 1212 of the strap may be pulled to separate it from the first section 1220 and positioned to engage with the user's forehead. The strap may accommodate, in side portions 1224 thereof, noise reduction components that are positionable over the user 10's ears when the headgear 1200 is worn.

In some forms, the noise reduction components 1224 may be larger (e.g., wider) than adjacent portions of the first section 1220, the second section 1214, and/or the third section 1212. This may reduce the total contact area on the user's head, while also allowing the noise reduction components 1224 to be wide enough to extend around the user's ears.

In some forms, the noise reduction components 1224 may protrude away from the surface of adjacent portions of the first section 1220, the second section 1212, and/or the third section 1214. This may provide adequate space to receive the user's ears.

Figure 13:
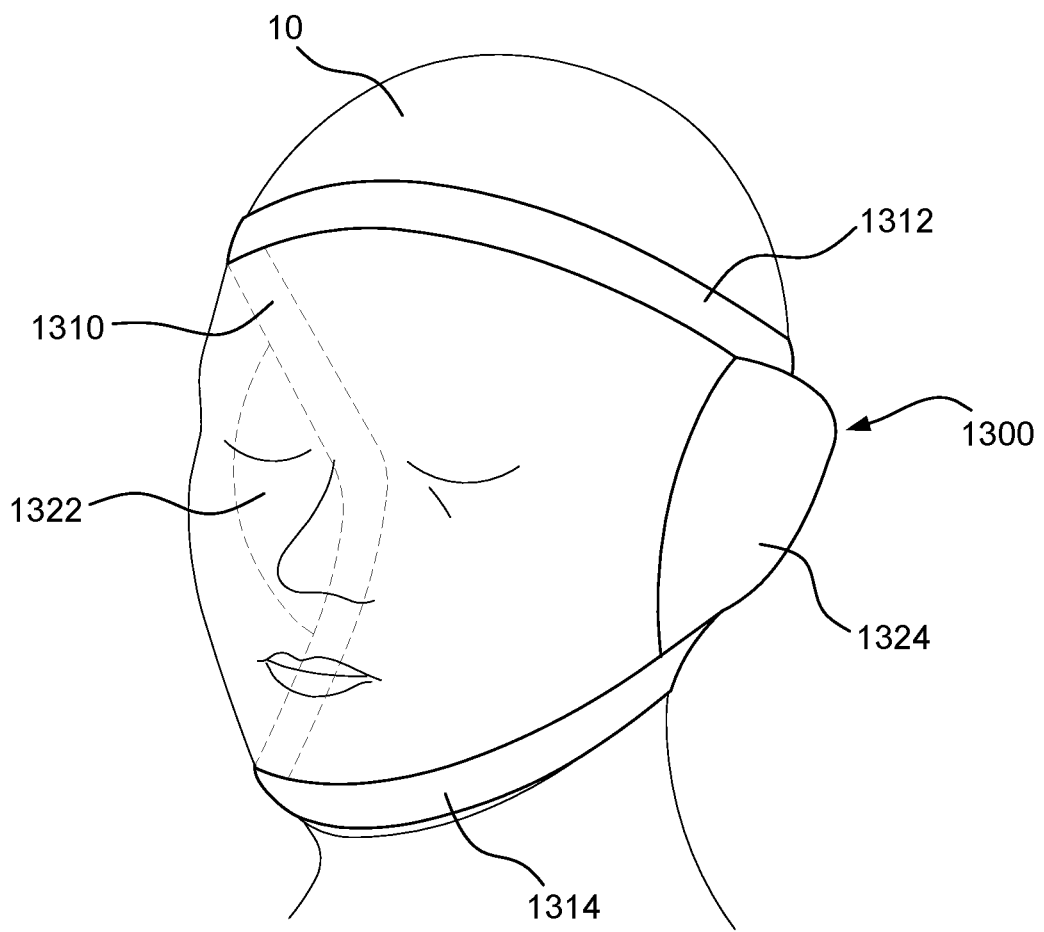
FIG. 13 shows headgear according to a further form of the present technology.

Another example of a headgear 1300 is shown in FIG. 13. In this example, the headgear 1300 comprises a single strap 1310 having a first section 1312 that engages with the user's forehead, and a second section 1314, connected to the first section 1312, that engages with the user's chin. For example, FIG. 13 illustrates the second section 1314 overlaying the user's mental protuberance. The strap incorporates a pair of noise reduction components 1322 and 1324 that fit over the ears of the user 10 when the headgear 1300 is worn. For example, the noise reduction components 1322 and 1324 may be incorporated between layers of the strap in enlarged sections thereof. The first section 1312 and second section 1314 can be sized to hold the noise reduction components in position at or in the ears. For example, the first section 1312 and second section 1314 can have the same thickness, or the first section 1312 can be thicker than the second section 1314, or the first section 1312 can be thinner than the second section 1314. Alternatively, the second section 1314 can further comprise a bifurcation each configured to engage the superior and inferior mental protuberance.

In some forms, the noise reduction components 1322, 1324 may be larger (e.g., wider) than adjacent portions of the first section 1312 and/or second section 1314 of the strap 1310. This may reduce the total contact area on the user's head, while also allowing the noise reduction components 1322, 1324 to be wide enough to extend around the user's ears.

In some forms, the noise reduction components 1322, 1324 may protrude away from the surface of adjacent portions of the first section 1312 and/or the second section 1314. This may provide adequate space to receive the user's ears.

Figure 14:
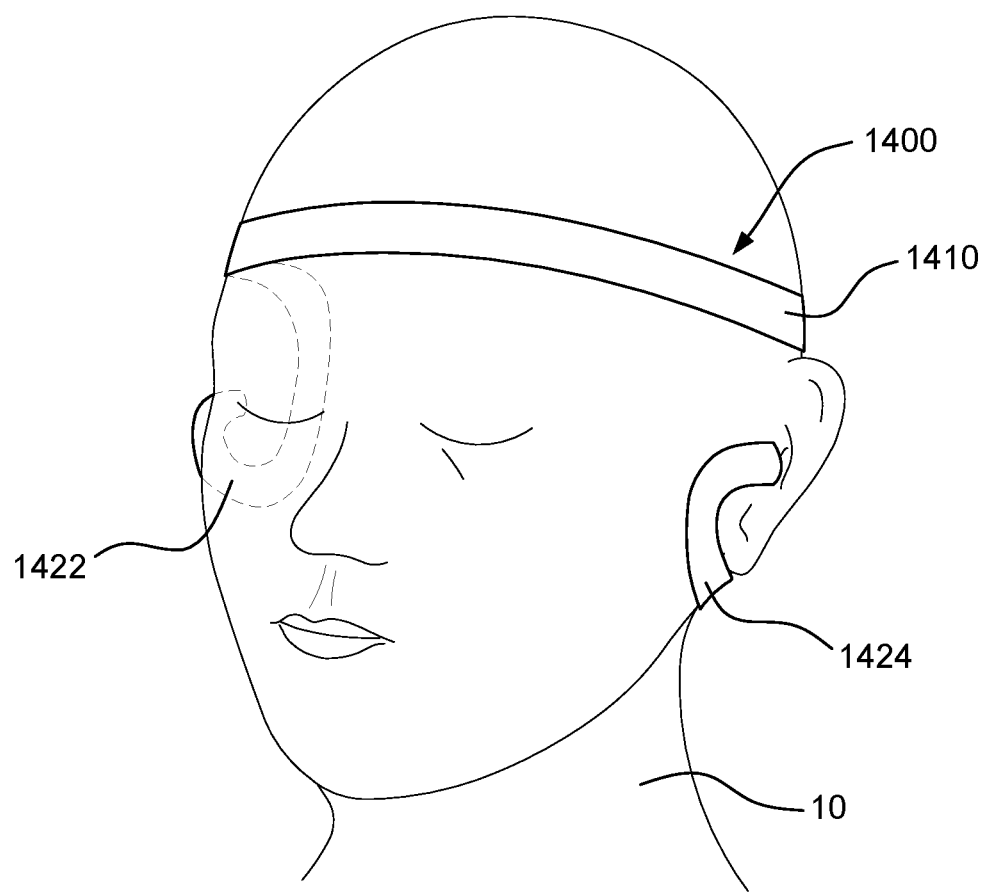
FIG. 14 shows headgear according to a further form of the present technology.

A further example of a headgear 1400 is shown in FIG. 14. In this example, a single strap 1410 formed from a textile material, which is at least partly resilient so as to enable easy fitting to the head of the user, has a pair of ear hooks 1422 and 1424 extending therefrom. Each ear hook 1422, 1424 carries a noise reduction component at an end thereof, which can be fitted into the user's ear to block external sound. The ear hooks 1422, 1424 may be formed from the same material as the strap 1410, but with rigidification to enable them to be supported on the user's ears.

Each of the example headgear devices 600, 800, 900, 1000, 1100, 1200, 1300, 1400 may be at least partly formed from a nonwoven textile material, and each may incorporate one or more electronic components, in like fashion to the headgear 400 of FIGS. 4 and 5.

In any of the noise-reduction components disclosed herein, one or more sensors and/or actuators may be incorporated into the noise-reduction component. For example, a noise-reduction component may comprise one or more microphones for detecting external noise and/or for detecting a noise level inside the user's ear (e.g., to determine the effectiveness of the noise-reduction component). A noise-reduction component may comprise one or more in-ear sensors for measuring physiological data such as temperature, EEG signals, heart rate, $SpO_2$ and the like. Further, a noise-reduction component may contain active noise-cancellation electronics and/or a speaker for generating sound, such as white noise, to assist with sleep.

In some forms, noise-cancellation electronics and/or a speaker may be paired with a smartphone, or other electronic device. For example, the user may be able to select a sound output using an application on the smartphone or other electronic device. The application may allow the user to select white noise, music, sleep meditation, or any other sound that may assist the user in falling asleep.

In some forms, the noise-cancellation electronics may operate without a smartphone application or other outside electronic device. For example, the noise-cancellation electronics may be contained on the headgear device.

In certain forms, the speaker may be connected to an external device. For example, a home alarm system (e.g., as a result of fire, carbon monoxide, a break-in, etc.) and/or a car alarm may be wirelessly connected to the speaker. Activation of either alarm may play a sound on the speaker to alert the user. The sound may override a noise otherwise selected by the user. When using noise-cancellation electronics, the activation of an alarm may automatically deactivate the noise-cancellation so that the user can hear the alarm.

Many modifications will be apparent to those skilled in the art without departing from the scope of the present invention.

Throughout this specification, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The invention claimed is:

1. A headgear, comprising:
a pair of noise reduction components each configured to fit over and/or at least partially inside respective ears of a user of the headgear, the pair of noise reduction components being coupled to a first strap, wherein the first strap is configured to retain the pair of noise reduction components in contact with the ears of the user;

wherein each noise reduction component of the pair of noise reduction components comprises a laminated structure that comprises at least one sound-reflecting layer, and at least one sound-absorbing layer that is arranged to be closer to the ear of the user than the at least one sound-reflecting layer; and wherein the pair of noise reduction components are each removably connected to headgear;

wherein each said noise reduction components at least partially defines a pocket configured to receive one ear of the user, said at least one sound-reflecting layer covering substantially all of said pocket; and wherein the first strap includes a front section configured to engage the user's frontal bone and a rear section configured to engage the back of the user's head.

2. The headgear of claim 1, wherein the first strap is resilient along at least part of its length.

3. The headgear of claim 2, wherein the first strap comprises one or more resilient sections and one or more non-stretchable sections.

4. The headgear of claim 1, wherein the first strap is formed by at least two separable sections that are movable relative to each other by way of a resilient member.

5. The headgear of claim 1, wherein the pair of noise reduction components are integrated with the first strap to form ear-covering portions thereof.

6. The headgear of claim 1, wherein the pair of noise reduction components are connected to the headgear via a hook-and-loop fastening mechanism, one or more magnets, and/or one or more clips.

7. The headgear of claim 1, wherein the pair of noise reduction components are located at respective ends of a second strap that is coupled to the first strap.

8. The headgear of claim 7, wherein the second strap comprises loops at the respective ends thereof, and wherein the first strap is configured to be threaded through the loops.

9. The headgear of claim 7, wherein the respective ends of the second strap are coupled to the first strap by a pivoting connection.

10. The headgear of claim 1, wherein the first strap comprises at least one bifurcation, such that a primary portion of the first strap is configured to engage with a forehead of the user, and one or more secondary portions of the first strap are configured to engage with a crown and/or chin of the user.

11. The headgear of claim 1, wherein the first strap comprises at least one layer of a non-woven textile material.

12. The headgear of claim 1, wherein the laminated structure comprises at least one layer of a non-woven textile material.

13. The headgear of claim 12, wherein the at least one layer of a non-woven textile material is directly connected to the at least one sound-absorbing layer.

14. The headgear of claim 1, wherein the at least one sound-absorbing layer comprises at least one layer of a sound-absorbing foam material.

15. The headgear of claim 14, wherein the sound-absorbing foam material is selected from one or more of: PE closed-cell foam; thermoplastic polyurethane foam; unbroken loop (UBL) fabric; UBL foam laminate; memory foam; EVA foam sheet; and fabric-foam-TPU-PU foam laminate.

16. The headgear of claim 1, wherein the at least one sound-reflecting layer comprises at least one of: a polymer film; a metallised polymer film; a metallised fabric; and/or a non-woven material.

17. The headgear of claim 1, wherein the laminated structure comprises at least one lamination layer constructed from a polyurethane film.

18. The headgear of claim 1, comprising one or more electronic components for monitoring, diagnosing and/or treating the user, the one or more electronic components being provided in, or on, the first strap.

19. The headgear of claim 8, comprising one or more electronic components for monitoring, diagnosing and/or treating the user, the one or more electronic components being provided in, or on, the second strap.

20. The headgear of claim 19, wherein the one or more electronic components comprise a wireless communications interface for transmitting data from the at least one sensor to one or more external computing devices, and/or for receiving data at the at least one actuator from the one or more external computing devices.

21. The headgear of claim 19, wherein the one or more electronic components comprise at least one sensor and/or at least one actuator.

22. The headgear of claim 21, wherein at least one sensor and/or at least one actuator is partly exposed to ambient at an exterior surface of the headgear; and/or is partly exposed at a user-contacting surface of the headgear.

23. The headgear of claim 21, wherein at least one sensor and/or at least one actuator is at least partly embedded between an outer layer and a user-contacting layer of the headgear.

24. The headgear of claim 21, wherein at least one sensor and/or at least one actuator comprises circuitry that is at least partially formed by one or more conductive threads, and/or one or more conductive ink traces.

25. The headgear of claim 21, wherein the at least one sensor and/or the at least one actuator comprise one or more of: an accelerometer; a gyroscope; a humidity sensor; a temperature sensor; a microphone; a camera; a pulse oximeter; an EEG sensor; an EMG sensor; an EOG sensor; a touch sensor; a vibration device; and an audio output device.

26. The headgear of claim 1, wherein the pair of noise reduction components are each larger than adjacent portions of the first strap.

27. The headgear of claim 1, wherein the pair of noise reduction components each protrude from a surface of the first strap.

28. The headgear of claim 1, wherein the at least one sound-reflecting layer directly contacts the at least one sound-absorbing layer.

29. The headgear of claim 28, wherein the at least one sound-reflecting layer is a first sound-reflecting layer and a second sound-reflecting layer, the at least one sound-absorbing layer is sandwiched between the first and second sound reflecting layers.

30. The headgear of claim 28, wherein the at least one sound-reflecting layer is a first sound-reflecting layer and a second sound-reflecting layer, the first sound-reflecting layer is sandwiched between the second sound-reflecting layer and the at least one sound-absorbing layer.

31. The headgear of claim 1, wherein the at least one sound-absorbing layer is substantially co-extensive with the at least one sound-reflecting layer and dimensioned and configured to cover the user's entire ear.

32. The headgear of claim 31, wherein each said noise reduction component at least partially defines a pocket configured to receive one ear of the user, said at least one sound-absorbing layer covering substantially all of said ear chamber.

33. The headgear of claim 31, wherein the laminated structure further includes:
   a non-woven layer connected to the at least one sound-absorbing layer,
   a fabric layer inside the non-woven layer and configured to be closest to the user; and
   a lamination layer connecting the non-woven layer and the fabric layer.

34. The headgear of claim 31, wherein the at least one sound-reflective layer comprises an aluminized PET sheet, the at least one sound-absorbing layer comprises a PE closed cell foam sheet, the non-woven layer includes sound-absorbing synthetic fibers, the fabric layer includes an unbroken loop fabric, and the lamination layer comprises a polyurethane film.

* * * * *